(12) United States Patent
Fan et al.

(10) Patent No.: US 11,718,872 B2
(45) Date of Patent: Aug. 8, 2023

(54) METHOD FOR OBTAINING SINGLE-CELL MRNA SEQUENCE

(71) Applicant: MGI TECH CO., LTD., Shenzhen (CN)

(72) Inventors: Fei Fan, Shenzhen (CN); Xiaofang Cheng, Shenzhen (CN); Wenwei Zhang, Shenzhen (CN); Weimao Wang, Shenzhen (CN); Luman Cui, Shenzhen (CN); Ou Wang, Shenzhen (CN)

(73) Assignee: MGI TECH CO., LTD., Shenzhen (CN)

( * ) Notice: Subject to any disclaimer, the term of this patent is extended or adjusted under 35 U.S.C. 154(b) by 308 days.

(21) Appl. No.: 16/909,366

(22) Filed: Jun. 23, 2020

(65) Prior Publication Data

US 2020/0318181 A1      Oct. 8, 2020

Related U.S. Application Data

(63) Continuation of application No. PCT/CN2018/124293, filed on Dec. 27, 2018.

(30) Foreign Application Priority Data

Dec. 28, 2017   (WO) ................ PCT/CN2017/119342

(51) Int. Cl.
*C12Q 1/6869*     (2018.01)
*C12Q 1/6818*     (2018.01)

(52) U.S. Cl.
CPC ......... *C12Q 1/6869* (2013.01); *C12Q 1/6818* (2013.01); *C12Q 2565/514* (2013.01)

(58) Field of Classification Search
CPC ................ C12Q 1/6869; C12Q 2565/514
See application file for complete search history.

(56) References Cited

U.S. PATENT DOCUMENTS

2016/0053253 A1    2/2016   Salathia et al.

FOREIGN PATENT DOCUMENTS

| CN | 104032377 A | 9/2014 |
|---|---|---|
| CN | 104350374 A | 2/2015 |
| CN | 106498040 A | 3/2017 |
| WO | 2014/201273 A1 | 12/2014 |

OTHER PUBLICATIONS

Islam et al. Genome Research. 2011. 21:1160-1167. (Year: 2011).*

(Continued)

*Primary Examiner* — Joseph G. Dauner
(74) *Attorney, Agent, or Firm* — Westman, Champlin & Koehler, P.A.; Z. Peter Sawicki; Amanda M. Prose

(57) ABSTRACT

A method for obtaining a single-cell mRNA sequence, including: (1) capturing mRNA of a cell by using a cell tag carrier, and performing reverse transcription to obtain cDNA having a cell tag; (2) obtaining multiple cDNA fragments having molecular tags by using a transposase complex and a molecular tag carrier; (3) performing high-throughput sequencing; (4) performing sequence assembly according to the molecular tags to obtain the sequence of each mRNA; and (5) obtaining the sequence of all mRNAs of each single cell according to the cell tags.

19 Claims, 11 Drawing Sheets

Specification includes a Sequence Listing.

(56) References Cited

OTHER PUBLICATIONS

Picelli et al. Nature Methods. 2013. 10(11):1096-1098 and Online Methods and Supplementary Items. (Year: 2013).*
Hashimshony et al. Genome Biology. 2016. 17:77, 7 pages (Year: 2016).*
Picelli et al. Nature Protocols. 2014. 9(1):171-181. (Year: 2014).*
Islam et al. Nature Methods. 2014. 11(2):163-166 and Online Methods. (Year: 2014).*
Tang et al. Nature Protocols. 2010. 5(3):516-535. (Year: 2010).*
Adey. Genome Research. 2021. 31:1693-1705. (Year: 2021).*
Picelli et al. Genome Research. 2014. 24:2033-2040. (Year: 2014).*
Pallares et al. G3. 2020. 10:143-150. (Year: 2020).*
Cole et al. Genome Research. 2020. 30:589-601. (Year: 2020).*
Trombetta et al. Current Protocols in Molecular Biology. 2014. 4.22.1-4.22.17. (Year: 2014).*
Search Report issued for EP Patent Application Serial No. 18896527.1, dated Aug. 9, 2021.
Hu, M. and Polyak, K. "Serial analysis of gene expression" (2006) Nature Protocols, vol. 1, No. 4, 1743-1760, retrieved from the internet, <http://www.nature.com/articles/nprot.2006.269>.
GenXPro, "Massive Analysis of cDNA Ends (MACE) Brochure", (2015), pp. 1-6, retrieved from the internet, <https://genxpro.net/wp-content/uploads/2015/07/MACE_GenXPro.pdf>.
International Search Report issued for PCT/CN2018/124293, dated Apr. 3, 2019.
Written Opinion of the International Searching Authority issued for PCT/CN2018/124293, dated Apr. 3, 2019.

* cited by examiner

METHOD FOR OBTAINING SINGLE-CELL MRNA SEQUENCE

CROSS-REFERENCE TO RELATED APPLICATION

This application is a U.S. continuation application of International Application No. PCT/CN2018/124293 filed on Dec. 27, 2018, which claims the priority of International Application No. PCT/CN2017/119342 filed on Dec. 28, 2017, the entire disclosure of which is incorporated herein by reference.

FIELD

The present disclosure relates to a method for obtaining mRNA sequence of a single cell.

BACKGROUND

Multicellular organism includes a variety of cell types as suggested by its name. In a multicellular organism, each cell type has its own unique function and such cell types with different functions get together to form tissues and organs, thereby as a whole defining the multicellular life. The lineage of each cell type and development status thereof determine the interaction between them with other cell types as well as surrounding microenvironment. More than that, different cells even classified in one same sub-cell type are probably to exhibit genetic heterogeneity.

The initial motivation of single-cell sequencing is mostly for cancer research. It is of great significance to research individual cells because different cells show a high degree of genetic specificity in the process of cancer development, and the difficulty in tumor sampling inevitably makes normal cells sampled. With the development of technology, single-cell sequencing technology has been widely useful in analyzing a complex biological system and process, such as the central nervous system, the immune system and mammalian development. Despite the unclear understanding about biological functions of tissues and organs in the single-cell level, single-cell sequencing and related analysis techniques provide a glimpse into the future.

In addition, single-cell sequencing provides a reliable means for identifying cells or organisms that are difficult to be in vitro isolated and cultured. The development of single-cell sequencing technology has improved the accuracy and sensitivity in detection of microbial pathogens in infectious diseases, and food transmitted or drug-resistant microbial pathogens, meanwhile it also provides solutions for diversity analysis of environmental or intestinal microbiome.

In recent years, high-throughput sequencing has rapidly developed, which becomes the optimum choice for single-cell DNA/RNA sequencing owing to its high accuracy and specificity. The early single-cell technique relied on micromanipulation or flow cytometry, with low throughput. The recent combination of microfluidic platform and water-in-oil technology has improved the cell detection throughput of single-cell mRNA sequencing to a very appreciable order of magnitude, however, it cannot sequence the full length of mRNA, therefore the differential splicing or gene fusion occurring in mRNAs cannot be detected. Further, the microfluidic chip has certain requirements for a control equipment, which further limits the expansion of its application.

Single-cell transcript sequencing is initially originated from the single-cell mRNA real-time quantitative PCR (qPCR) detection technology which determines the technical basis of transcript amplification. Subsequently, with the development of high-throughput sequencing platforms, single-cell transcript sequencing has also emerged. The earliest single-cell isolation procedure relies on a mouth pipette to isolate a single cell from a cell population, which can realize detection of full-length transcripts, but it has a high requirement on experimental personnel and has a low throughput of test cells. After that, researchers have developed a single-cell isolation method based on laser microdissection. However, such a method requires to be conducted on an expensive device and damages the activity of cut cells to a certain extent thus affecting the downstream experimental results. Then, flow cytometry-based single-cell isolation method is developed, but it has to be conducted on an expensive device and damages the activity of cells to be isolated to a certain extent similar to the laser microdissection method. Fluidigm introduced a C1 single-cell sequencing system, which captures individual cells into special chambers by using its own developed microfluidic chip, thus achieving the single-cell separation effect. However, the C1 single-cell sequencing system of Fluidigm is expensive (800 dollars per run) and enables a single-cell processing throughput of 96 cells per run, which is not cost-advantageous. Even Fluidigm has planed to update the system to 384 cells per run, but the corresponding cost is also increased. In 2015, a single-cell isolation method based on microfluidic/water-in-oil droplets and a carrier with a cell tag is developed, which greatly increases the test number of single cells at one time. However, since the cell tag in the carrier is connected to oligo(dT) served for reverse transcription, the microfluidic/water-in-oil droplet method can only obtain the sequence of 3' end of mRNA rather than full-length of mRNA at single-cell mRNA sequencing under the limitation of short reads of next-generation sequencing.

SUMMARY

The present disclosure in embodiments provides a method for obtaining sequences of mRNA molecules of a single cell.

The present disclosure in embodiments provides a method for obtaining sequences of mRNA molecules of a single cell, comprising the steps of:

(a) utilizing a carrier with cell tag to capture mRNA molecules of the single cell, followed by performing a reverse transcription reaction to obtain cDNA molecules with cell tags, (b) utilizing a transposase complex and a carrier with molecule tag to obtain cDNA fragments with molecule tags, (c) high-throughput sequencing the cDNA fragments with the molecule tags obtained in step (b), and (d) assembling sequencing results obtained in step (c) to obtain sequence of each mRNA molecule according to the molecule tag and obtaining sequences of all the mRNA molecules in each single cell according to the cell tag, wherein the carrier with cell tag is a solid carrier carrying a cell tag, the carrier with molecule tag is a solid carrier carrying a molecule tag, each cDNA molecule derived from one same single cell has a same cell tag and the cDNA molecules derived from different single cells have different cell tags, and all the cDNA fragments derived from one same cDNA molecule have a same molecule tag and the cDNA fragments derived from different cDNA molecules have different molecule tags.

The present disclosure in embodiments provides a method for obtaining and quantifying mRNA molecules of a single cell, comprising the steps of:
  (a) utilizing a carrier with cell tag to capture mRNA molecules of the single cell, followed by performing a reverse transcription reaction to obtain cDNA molecules with cell tags and transcript tags,
  (b) utilizing a transposase complex and a carrier with molecule tag to obtain cDNA fragments with molecule tags,
  (c) high-throughput sequencing the cDNA fragments with the molecule tags obtained in step (b), and
  (d) assembling sequencing results obtained in step (c) to obtain sequence of each mRNA molecule according to the molecule tag, obtaining all the mRNA molecules in each single cell according to the cell tag, and quantifying each mRNA molecule in each single cell according to the sequence count having different transcript tags and a same mRNA sequence,
  wherein the carrier with cell tag is a solid carrier carrying a cell tag and a transcript tag,
  the carrier with molecule tag is a solid carrier carrying a molecule tag,
  each cDNA molecule derived from one same single cell has a same cell tag and the cDNA molecules derived from different single cells have different cell tags, and the cDNA molecules derived from the same single cell each have a different transcript tag, and
  all the cDNA fragments derived from one same cDNA molecule have a same molecule tag and the cDNA fragments derived from different cDNA molecules have different molecule tags.

The present disclosure in embodiments provides a method for preparing a single-cell derived cDNA sequencing library, comprising the steps of:
  (a) obtaining cDNA molecules with cell tags, where each cDNA molecule derived from one same single cell has a same cell tag and the cDNA molecules derived from different single cells have different cell tags, and
  (b) obtaining cDNA fragments with molecule tags, where all the cDNA fragments derived from one same cDNA molecule have a same molecule tag and the cDNA fragments derived from different cDNA molecules have different molecule tags.

The step of obtaining cDNA molecules with cell tags is performed by utilizing a carrier with cell tag to capture mRNA molecules of the single cell, followed by performing a reverse transcription reaction to obtain cDNA molecules with the cell tags, wherein the carrier with cell tag is a solid carrier carrying a cell tag.

The step of obtaining cDNA fragments with molecule tags is performed by utilizing a transposase complex and a carrier with molecule tag to obtain the cDNA fragments with the molecule tags, wherein the carrier with molecule tag is a solid carrier carrying a molecule tag.

The present disclosure in embodiments provides a method for preparing a quantifiable single-cell derived cDNA sequencing library, comprising the steps of:
  (a) obtaining cDNA molecules with cell tags and transcript tags, where each cDNA molecule derived from one same single cell has a same cell tag and the cDNA molecules derived from different single cells have different cell tags, and the cDNAs derived from the same single cell each have a different transcript tag, and
  (b) obtaining cDNA fragments with molecule tags, where all the cDNA fragments derived from one same cDNA molecule have a same molecule tag and the cDNA fragments derived from different cDNA molecules have different molecule tags.

Specifically, the step of obtaining cDNA molecules with cell tags and transcript tags is performed by utilizing a carrier with cell tag to capture mRNA molecules of the single cell, followed by performing a reverse transcription reaction to obtain cDNA molecules with the cell tags and the transcript tags, wherein the carrier with cell tag is a solid carrier carrying a cell tag and a transcript tag.

Specifically, the step of obtaining cDNA fragments with molecule tags is performed by utilizing a transposase complex and a carrier with molecule tag to obtain the cDNA fragments with the molecule tags, wherein the carrier with molecule tag is a solid carrier carrying the molecule tag.

Specifically, the method further comprises a step of enriching the cDNA molecules with the cell tags between step (a) and step (b). The step of enriching the cDNA molecules with the cell tags between step (a) and step (b) may be specifically a PCR amplification reaction or a rolling circle amplification, or other reaction means known to skilled in the art.

Specifically, the method further comprises a step of enriching the cDNA fragments with the molecule tags between step (b) and step (c).

Specifically, the step (b) comprises incubating the cDNA molecules with the cell tags with the transposase complex to obtain a complex of cDNA molecule linked with the transposase complex.

Specifically, the step (b) further comprises utilizing the carrier with molecule tag to capture the complex of cDNA molecule linked with the transposase complex as described above to make all the cDNA fragments carried with the molecule tags, and releasing the cDNA fragments with the molecule tags.

The present disclosure in embodiments provides a kit for preparing a single-cell derived cDNA sequencing library, comprising: a carrier with cell tag, wherein the carrier with cell tag is a solid carrier carrying a cell tag for obtaining cDNA molecules with the cell tags, and a carrier with molecule tag, wherein the carrier with molecule tag is a solid carrier carrying a molecule tag for obtaining cDNA fragments with molecule tags, wherein each cDNA molecule derived from one same single cell has a same cell tag and the cDNA molecules derived from different single cells have different cell tags, and all the cDNA fragments derived from one same cDNA molecule have a same molecule tag and the cDNA fragments derived from different cDNA molecules have different molecule tags.

The present disclosure in embodiments provides a kit for preparing a quantifiable single-cell derived cDNA sequencing library, comprising: a carrier with cell tag, wherein the carrier with cell tag is a solid carrier carrying a cell tag and a transcript tag for obtaining cDNA molecules with the cell tags and the transcript tags, and a carrier with molecule tag, wherein the carrier with molecule tag is a solid carrier carrying a molecule tag for obtaining cDNA fragments with molecule tags, wherein each cDNA molecule derived from one same single cell has a same cell tag and the cDNA molecules derived from different single cells have different cell tags, and the cDNAs derived from the same single cell each have a different transcript tag, and all the cDNA fragments derived from one same cDNA molecule have a same molecule tag and the cDNA fragments derived from different cDNA molecules have different molecule tags.

Specifically, the kit further comprises a transposase complex. The transposase complex consists of a transposon and a transposase.

Specifically, the kit also comprises a primer for the reverse transcription reaction.

Specifically, the kit also comprises a blocking sequence and a primer for conducting utilizing a transposase complex and a carrier with molecule tag to obtain a various of cDNA fragments with molecule tags.

Specifically, the kit also comprises a primer pair for conducting the PCR amplification to obtain a sequencing library.

Specifically, the kit also comprises a single-stranded oligonucleotide for conducting the cyclization reaction and the rolling circle amplification.

Specifically, the kit also comprises a primer for conducting the cyclization reaction and the rolling circle amplification.

Specifically, the kit also comprises a primer for synthesizing the second strand of a rolling circle amplification product.

Specifically, the kit also comprises a microwell chip or a microfluidic droplet system.

As one specific embodiment, the carrier with cell tag is prepared by connecting a multiple of DNA molecules II to the surface of the solid carrier, the DNA molecule II is a partially double-stranded structure composed of a third single-stranded DNA molecule and a fourth single-stranded DNA molecule, and the DNA molecule II comprises the cell tag and an mRNA capture region.

As another specific embodiment, the carrier with cell tag is prepared by connecting a multiple of DNA molecules II to the surface of the solid carrier, the DNA molecule II is a partially double-stranded structure composed of a third single-stranded DNA molecule and a fourth single-stranded DNA molecule, and the DNA molecule II comprises a cell tag, a transcript tag and an mRNA capture region.

The carrier with cell tag may also be other forms known to skilled in the art.

The transcript tags of the DNA molecules II connected to different carriers with cell tag may be same or different.

The carrier with molecule tag is prepared by connecting a multiple of DNA molecules I to the surface of the solid carrier, the DNA molecule I is a partially double-stranded structure composed of a first single-stranded DNA molecule and a second single-stranded DNA molecule, and the DNA molecule I comprises the molecule tag and a transposase complex capture region.

The carrier with molecule tag may also be other forms known to skilled in the art.

The present disclosure in embodiments also provides use of the method as described above in high-throughput obtaining all the mRNA molecules of each single cell in a large number of single cells.

The present disclosure in embodiments also provides use of the method as described above in high-throughput obtaining and quantifying all the mRNA molecules of each single cell in a large number of single cells.

The present disclosure in embodiments also provides use of the kit as described above in high-throughput obtaining all the mRNA molecules of each single cell in a large number of single cells.

The present disclosure in embodiments also provides use of the kit as described above in high-throughput obtaining and quantifying all the mRNA molecules of each single cell in a large number of single cells.

In view of the limitations and deficiencies of the current single-cell mRNA sequencing products on the market, the present disclosure in embodiments proposes a method based on short-reads co-tagging (i.e. co-barcoding), which is expected to solve the problem of the current high-throughput technology, such as unable to detect full-length mRNA transcripts or low throughput for successful detected full-length transcripts.

In the present disclosure, single cells are separated through the single-cell separation technology and cDNA molecules derived from the single cell are added with a cell tag. Each full-length cDNA molecule by reverse transcription is tagged with one kind of molecule tag according to the virtual separation and the molecule tag co-barcoding technology. Subsequently, short reads carrying a same molecule tag are assembled to restore the original full-length cDNA according to the cell tag carried at the end of cDNA molecules and the molecule tag carried at the end of cDNA fragments. After that, the cell origin of each cDNA molecule can be determined via the cell tag. That is, the molecule origin and the cell origin of single-cell derived cDNAs are respectively recorded by a dual labeling system, thereby overcoming the problem of unable to sequence the full-length cDNA due to the lacking of cell tag during the conventional high-throughput single-cell RNA sequencing.

The principle of the present disclosure is: single cells are separated by a microwell chip (or a microfluidic droplet system), and the cell tag carrier is arranged in the microwell (or droplet) containing a single cell. The single cells are lysed and mRNA molecules in the single cell are released. The reverse transcription primer carrying the cell tag on the surface of the cell tag carrier captures the mRNA molecules, followed by a reverse transcription reaction to obtain full-length cDNA molecules with the cell tags at its 3' end. Subsequently, the full-length cDNA molecules in a same virtual compartment are labeled by using a same kind of molecule barcode based on the virtual compartments and the fast enzyme reaction, followed by routine library construction and sequencing. When the cDNA number in a virtual compartment is small, it is considered that the sequenced reads having a same molecule tag are from a same cDNA molecule, thus short reads generated by the sequencer can be denovo assembled to restore the original cDNA sequence according to the molecule tag after sequencing is completed. After that, the cell origin of each full-length cDNA molecule can be determined via the cell tag at the 3' end of the cDNA, thereby realizing the detection of single-cell full-length cDNA.

The key inventiveness of the present disclosure lies in below.

(1) Microwell Chip Based Single-Cell Separation Technology

This technology is established on the theory that random sampling of a large number of samples ultimately obeys the Poisson distribution. When a limited amount of diluted cells are added to a microwell chip with a sufficient number of wells, most wells would not contain cells, a small number of wells contain one cell and very few wells contain two or more cells. Subsequently, microsphere carriers in a diameter equivalent to the microwell and carry a specific nucleic acid sequence (cell tag) for labeling messenger RNA (i.e. mRNA) in a single cell are added, in which the specific nucleic acid sequence is used to label the cell origin of mRNA in the single cell. Each well can only contain one microsphere carrier due to the limitation of the diameter of the microwell, thus achieving the effect that one single cell is only labeled with one kind of cell tag.

(2) Virtual Separation Based Labeling Technology

The range of molecular thermal motion is limited within a certain period of time due to relatively stable rate of molecular thermal motion, thus the liquid space within a certain radius can be regarded as "virtual" separation. When the liquid volume is large enough and the molecule number is small enough, the distance between the molecules is large, thus two independent molecules can be considered as completely isolated without interaction. All the mRNA molecules in each single cell are individually labeled with cell tags, followed by a reverse transcription reaction to form the cDNA molecules with cell tags. After that, a carrier with molecule tag is added into the single reaction system to make the cDNA molecules virtually separated, followed by fragmentation and tagging process, thereby all the short reads from a same cDNA molecule are labeled with a same kind of molecule tag, and thus finally realizing a dual labeling system.

DETAILED DESCRIPTION

Figure 1:
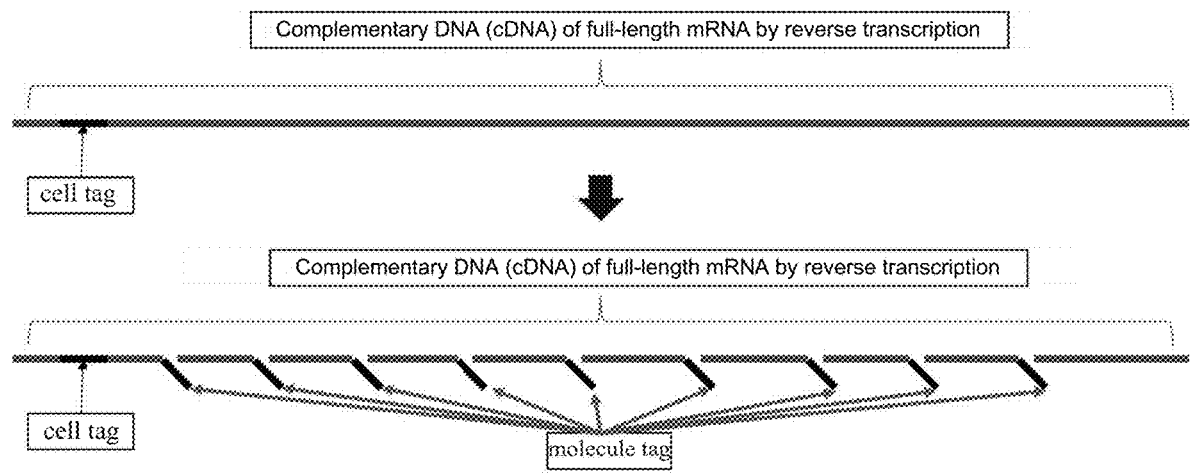
FIG. 1 is a schematic diagram of the method provided in the present disclosure.

The following embodiments facilitate a better understanding of the present disclosure, but they do not limit the present disclosure. Unless otherwise specified, the experimental methods in the following examples are all conventional methods. Unless otherwise specified, the test materials used in the following examples are all purchased from conventional biochemical reagent companies. In the following quantitative experiments, three repeats are conducted and results are averaged.

In a specific embodiment of the present disclosure, a chip with a large number of microwells is prepared. After that, a limited amount of cells are added to the surface of the microwell chip, and the excess cells on the surface of the microwell chip that do not enter into the microwells are washed away after the cells have fully settled into the microwells. Then a specially designed mRNA capture carrier carrying a cell tag is added and the cells are lysed in situ in the well, such that the mRNA capture carrier carrying the cell tag captures the mRNAs released by the cell in the well; mRNAs in wells are subjected to the reverse transcription reaction or the solution containing the mRNA capture carriers is collected to a reaction vessel to perform the mRNA reverse transcription reaction, thereby generating the corresponding full-length cDNAs with cell tag at one end. Subsequently, a certain amount of full-length cDNA molecules are mixed with transposase complexes, such that the transposase complex is randomly inserted into and bound to the full-length cDNA molecule at a certain temperature. Afterwards, the full-length cDNA molecules with the transposase complex are incubated with a carrier carrying a large number of specific molecule tags (i.e. barcodes), in which the carrier is capable of capturing the transposase complex bound to the full-length cDNA molecule, and then the reaction volume, cDNA molecule concentration, carrier concentration and reaction time are controlled, such that each carrier with a large number of the specific molecule tags (i.e. barcodes) forms a virtual compartment, therefore cDNA molecules can fall into the virtual compartments formed by one carrier when the amount of the full-length cDNA molecules is low enough and the number of carriers with a large number of the specific molecule tags is sufficient enough, as such one carrier can capture one cDNA molecule only. After the cDNA molecule is captured by the carrier with molecule tag, the barcode in the carrier would be connected to the adaptor sequence of the transposase complex, as such the barcode in the carrier with molecule tag can be transferred to the cDNA molecule. After that, the transposase is released, and the full-length cDNA is fragmented into short sequences suitable for sequencing, in which the short sequences from one same full-length cDNA molecule carry a same specific molecule tag. Then, short reads generated by sequencing are assembled to restore the original full-length cDNA according to the specific molecule tags, and the cell origin of each cDNA molecule is determined via the cell tag and the molecule tag carried in the cDNA molecule, thereby achieving the high-throughput single-cell full-length transcript sequencing.

The embodiment as described above can be implemented through four steps. The first step includes preparing a large number of carriers with multiple copies of specific cell tags and a large number of carriers with multiple copies of specific molecule tags; the second step includes distributing single cells into individual microwells and utilizing the carrier with the cell tag to capture mRNAs in a single cell such that one carrier with one kind of cell tag captures mRNAs in one single cell; the third step includes combining the cDNA formed by reverse transcription with a transposase complex; and the fourth step includes utilizing the carrier with the molecule tag to capture a full-length cDNA with the transposase complex and making the molecule tag in the carrier transferred into the cDNA sequence.

In a specific embodiment, the carrier with cell tag is prepared by connecting a multiple of DNA molecules II to the surface of a solid carrier. The DNA molecule II is a partially double-stranded structure composed of a third single-stranded DNA molecule and a fourth single-stranded DNA molecule. The third single-stranded DNA molecule consists of the following three regions in sequence from the 5'→3' direction: a 5' end region, a middle region and a 3' end region. The fourth single-stranded DNA molecule is entirely reverse complementary with the middle region of the third single-stranded DNA molecule to form the partially double-stranded structure. The 5' end of the third single-stranded DNA molecule is connected to the surface of the solid carrier of the carrier with cell tag. The 3' end region of the third single-stranded DNA molecule comprises an mRNA capture region. The middle region of the third single-stranded DNA molecule comprises a cell tag. In practice, the 3' end of the third single-stranded DNA molecule can be connected to the surface of the solid carrier of the carrier with cell tag.

In another specific embodiment, the carrier with cell tag is prepared by connecting a multiple of specific DNA molecules II to the surface of a solid carrier. The specific DNA molecule II is a partially double-stranded structure composed of a third single-stranded DNA molecule and a fourth single-stranded DNA molecule. The third single-stranded DNA molecule consists of the following three regions in sequence from the 5'→3' direction: a 5' end region, a middle region and a 3' end region. The fourth single-stranded DNA molecule is entirely reverse complementary with the middle region of the third single-stranded DNA molecule to form the partially double-stranded structure. The 5' end of the third single-stranded DNA molecule is connected to the surface of the solid carrier of the carrier with cell tag. The 3' end region of the third single-stranded DNA molecule comprises a unique transcript tag and an mRNA capture region in sequence from the 5'→3' direction. The middle region of the third single-stranded DNA molecule comprises a cell tag. In practice, the 3' end of the third single-stranded DNA molecule can be connected to the surface of the solid carrier of the carrier with cell tag.

In a specific embodiment, the carrier with molecule tag is prepared by connecting a multiple of DNA molecules I to the surface of a solid carrier. The DNA molecule I is a partially double-stranded structure composed of a first single-stranded DNA molecule and a second single-stranded DNA molecule. The first single-stranded DNA molecule consists of the following three regions in sequence from the 5'→3' direction: a 5' end region, a middle region and a 3' end region. The second single-stranded DNA molecule is entirely reverse complementary with the middle region of the first single-stranded DNA molecule to form the partially double-stranded structure. The 5' end region of the first single-stranded DNA molecule comprises a transposase complex capture region. The 3' end of the first single-stranded DNA molecule is connected to the surface of the solid carrier of the carrier with molecule tag. The middle region of the first single-stranded DNA molecule comprises a molecule tag. In practice, the 5' end of the first single-stranded DNA molecule can be connected to the surface of the solid carrier of the carrier with molecule tag.

In a specific embodiment, the solid carrier is in a granular form. The granular solid carrier may specifically be magnetic beads, colloidal beads, silica beads or the like.

In a specific embodiment, for the carrier with cell tag, the surface of each granular solid carrier is connected to DNA molecules II belonging to one same type which has a same nucleotide sequence. The surface of each granular solid carrier is connected to a large number of the DNA molecules II belonging to the same type, particularly 10,000,000 or more DNA molecules II, preferably 100,000,000 or more DNA molecules II, more preferably 500,000,000 or more DNA molecules II.

In a specific embodiment, for the carrier with molecule tag, the surface of each granular solid carrier is connected to DNA molecules I belonging to one same type which has a same nucleotide sequence. The surface of each granular solid carrier is connected to a large number of DNA molecules I belonging to the same type, particularly 10,000 or more DNA molecules I, preferably 50,000 or more DNA molecules I, more preferably 80,000 or more DNA molecules I.

Specifically, 500,000 or more kinds of cell tags, preferably 1,000,000 or more kinds of cell tags, and more preferably 2,000,000 or more kinds of cell tags can be used. The carrier with cell tag may have one or more sets of cell tags, such as two sets of cell tags, three sets of cell tags and the like to increase the cell type which can be tagged by the cell tag. In a specific embodiment, the cell tag consists of a cell tag 1, a spacer sequence and a cell tag 2. The cell tag 1 may consist of 4 to 50 nucleotides, preferably 8 to 20 nucleotides. The cell tag 1 is designed based on the principle of synthesis by four nucleotides (A, T, C and G) and avoidance of three or more consecutive same and single nucleotides. The cell tag 2 may consist of 4 to 50 nucleotides, preferably 8 to 20 nucleotides. The cell tag 2 is designed based on the principle of synthesis by four nucleotides (A, T, C and G) and avoidance of three or more consecutive same and single nucleotides. In particular, the cell tag 1 may consist of 10 nucleotides, and the cell tag 2 may consist of 10 nucleotides. In particular, 1536 kinds of the cell tags 1 and 1536 kinds of the cell tags 2 can be used, thus capable of obtaining 2,359,296 kinds of cell tag combinations. In particular, 768 kinds of the cell tags 1 and 384 kinds of the cell tags 2 can be used, thus capable of obtaining 294,912 kinds of cell tag combinations.

Specifically, 500,000 or more kinds of molecule tags, preferably 1,000,000 or more kinds of molecule tags, and more preferably 2,000,000 or more kinds of molecule tags can be used. The carrier with molecule tag may have one or more sets of molecule tags, such as two sets of molecule tags, three sets of molecule tags and the like to increase the molecule type which can be tagged by the molecule tag. In a specific embodiment, the molecule tag consists of a molecule tag 1, a spacer sequence and a molecule tag 2. The molecule tag 1 may consist of 4 to 50 nucleotides, preferably 8 to 20 nucleotides. The molecule tag 1 is designed based on the principle of synthesis by four nucleotides (A, T, C and G) and avoidance of three or more consecutive same and single nucleotides. The molecule tag 2 may consist of 4 to 50 nucleotides, preferably 8 to 20 nucleotides. The molecule tag 2 is designed based on the principle of synthesis by four nucleotides (A, T, C and G) and avoidance of three or more consecutive same and single nucleotides. In particular, the molecule tag 1 may consist of 10 nucleotides, and the molecule tag 2 may consist of 10 nucleotides. In particular, 1536 kinds of the molecule tags 1 and 1536 kinds of the molecule tags 2 can be used, thus capable of obtaining 2,359,296 kinds of molecule tag combinations. In particular, 768 kinds of the molecule tags is and 384 kinds of the molecule tags 2 can be used, thus capable of obtaining 294,912 kinds of molecule tag combinations.

The unique transcript tag may consist of 8 to 50 nucleotides, for example, 8 to 20 nucleotides, in which each nucleotide is a random A, T, C or G. As a specific embodiment, the unique transcript tag consists of 10 nucleotides.

As a specific embodiment, in reverse transcription reaction, the TSO primer used is shown in SEQ ID NO: 13 of the sequence listing and the ISO primer used is shown in SEQ ID NO: 14 of the sequence listing.

As a specific embodiment, in "utilizing a transposase complex and a carrier with molecule tag to obtain a various of cDNA fragments with molecule tags", the blocking sequence used is shown in SEQ ID NO: 19 of the sequence listing, and the primer used is shown in SEQ ID NO: 20 of the sequence listing.

As a specific embodiment, in "PCR amplification", a primer pair used consists of a first primer shown in SEQ ID NO: 21 of the sequence listing and a second primer shown in SEQ ID NO: 22 of the sequence listing.

As a specific embodiment, "utilizing a carrier with cell tag to capture mRNAs of a single cell" is performed in a microwell chip or a microfluidic droplet system. The microwell in the microwell chip may specifically have a diameter of 25 μm and a height of 30 μm. The number of microwells in each microwell chip may be 10,000 or above, preferably 100,000.

As a specific embodiment, for the carrier with cell tag, the surface of each granular solid carrier may be specifically connected to 10,000,000 or more, preferably 100,000,000 or more, more preferably 500,000,000 or more of the DNA molecules II.

As a specific embodiment, the primers for reverse transcription reaction include a TSO primer and an ISO primer. The TSO primer is shown in SEQ ID NO: 13 of the sequence listing. The ISO primer is shown in SEQ ID NO: 14 of the sequence listing.

As a specific embodiment, the blocking sequence is shown in SEQ ID NO: 19 of the sequence listing and the primer used is shown in SEQ ID NO: 20 of the sequence listing.

As a specific embodiment, in the PCR amplification to obtain the sequencing library, the primer pair used consists of a primer shown in SEQ ID NO: 21 of the sequence listing and a primer shown in SEQ ID NO: 22 of the sequence listing.

As a specific embodiment, the primer for reverse transcription reaction is a TSO primer. The TSO primer specifically used in the embodiment may be shown in SEQ ID NO: 13 of the sequence listing. As a specific embodiment, the primer used for PCR amplification to obtain the full-length transcript amplification product is an ISO primer. The ISO primer specifically used in the embodiment may be shown in SEQ ID NO: 23 of the sequence listing. As a specific embodiment, the single-stranded oligonucleotide used for rolling circle amplification is Oligo. The Oligo specifically used in the embodiment may be shown in SEQ ID NO: 24 of the sequence listing. The primer used for synthesis of double-stranded structure in the embodiment may be specifically shown in SEQ ID NO: 21 of the sequence listing.

As a specific embodiment, the primer for reverse transcription reaction is a TSO primer. The TSO primer specifically used in the embodiment may be shown in SEQ ID NO: 25 of the sequence listing. As a specific embodiment, the primers used for PCR amplification to obtain the full-length transcript amplification product are an ISO primer and a PCR primer. The ISO primer specifically used in the embodiment may be shown in SEQ ID NO: 26 of the sequence listing. The PCR primer specifically used in the embodiment may be shown in SEQ ID NO: 27 of the sequence listing. As a specific embodiment, the single-stranded oligonucleotide used for single-strand cyclization reaction is Oligo, and the Oligo specifically used in the embodiment may be shown in SEQ ID NO: 28 of the sequence listing. As a specific embodiment, the single-stranded oligonucleotide used for rolling circle amplification is Oligo, and the Oligo specifically used in the embodiment may be shown in SEQ ID NO: 27 of the sequence listing. The primer used for synthesis of double-stranded structure in the embodiment may be specifically shown in SEQ ID NO: 21 of the sequence listing.

As a specific embodiment, the microwell in the microwell chip may have a diameter of 25 μm and a height of 30 μm.

As a specific embodiment, the number of microwells in each microwell chip is 10,000 or above, preferably 100,000.

The mRNA capture region may consist of 17 to 25 consecutive T bases and a V base at the 3' end.

The transposase complex specifically consists of a transposon 1, a transposon 2 and a transposase. The transposon 1 can be captured by the transposase complex capture region, and the transposon 2 cannot be captured by the transposase complex capture region. The transposase may specifically be Tn5 transposase.

As a more specific embodiment, the specific DNA molecule II is specifically obtained by connecting a fragment L2, a fragment 3 and a fragment 4 in sequence, in which the fragment L2 is obtained by annealing a single-stranded DNA shown in SEQ ID NO: 7 of the sequence listing and a single-stranded DNA shown in SEQ ID NO: 8 of the sequence listing, the fragment 3 is obtained by annealing a single-stranded DNA shown in SEQ ID NO: 9 of the sequence listing and a single-stranded DNA shown in SEQ ID NO: 10 of the sequence listing, and the fragment 4 is obtained by annealing a single-stranded DNA shown in SEQ ID NO: 11 of the sequence listing and a single-stranded DNA shown in SEQ ID NO: 12 of the sequence listing. In this specific embodiment, the carrier with cell tag is obtained by connecting the 5' sticky end of the specific DNA molecule II to the surface of the solid carrier.

As a more specific embodiment, the specific DNA molecule I is specifically obtained by connecting a fragment 2, a fragment 1 and a fragment L1 in sequence, in which the fragment 2 is obtained by annealing a single-stranded DNA shown in SEQ ID NO: 5 of the sequence listing and a single-stranded DNA shown in SEQ ID NO: 6 of the sequence listing, the fragment 1 is obtained by annealing a single-stranded DNA shown in SEQ ID NO: 3 of the sequence listing and a single-stranded DNA shown in SEQ ID NO: 4 of the sequence listing, and the fragment L1 is obtained by annealing a single-stranded DNA shown in SEQ ID NO: 1 of the sequence listing and a single-stranded DNA shown in SEQ ID NO: 2 of the sequence listing. In this specific embodiment, the carrier with molecule tag is obtained by connecting the 3' sticky end of the specific DNA molecule I to the surface of the solid carrier.

As a more specific embodiment, the transposon 1 is obtained by annealing a single-stranded DNA shown in SEQ ID NO: 15 of the sequence listing and a single-stranded DNA shown in SEQ ID NO: 16 of the sequence listing. As a more specific embodiment, the transposon 2 is obtained by annealing a single-stranded DNA shown in SEQ ID NO: 17 of the sequence listing and a single-stranded DNA shown in SEQ ID NO: 18 of the sequence listing.

Working solution of ligation buffer: 10 g/100 mL $PEG_{8000}$, 50 mM Tris-HCl, 0.33 mM ATP, 0.05 mg/mL BSA, 10 mM $MgCl_2$, 0.5 mM DTT, and water as the balance.

Low-salt magnetic bead washing buffer: 50 mM Tris-HCl, 150 mM NaCl, 0.02% (by volume) Tween-20 (Polysorbate 20), and water as the balance.

High-salt magnetic bead washing buffer: 50 mM Tris-HCl, 500 mM NaCl, 0.02% (by volume) Tween-20, and water as the balance.

Carrier loading buffer: 0.1% (by volume) Tween-20, and 1M phosphate buffer saline buffer (PBS buffer, pH 8.0) as the balance.

Cell lysis buffer: 14 mM NaCl, 3 mM KCl, 1 mM EDTA, 12 g/100 mL sucrose, 1% (by volume) Triton X-100, and 13 mM Tris-HCl buffer (pH 7.5) as the balance.

Washing buffer: 150 mM NaCl, 0.02% (by volume) Tween-20, and 50 mM Tris-HCl buffer (pH 7.5) as the balance.

Reverse transcription buffer: 75 mM KCl, 3 mM MgCl$_2$, and 50 mM Tris-HCl buffer (pH 8.3) as the balance.

Tn5 transposase is purchased from Nanjing Nuoweizan Company, with a product name of TruePrep Advanced DNA Sample Prep Kit and a catalog number of S301-01.

Example 1 Establishment of Method

The schematic diagram of the technical process is shown in FIG. 1.

1. Preparation of a molecule tag carrier

Figure 2:
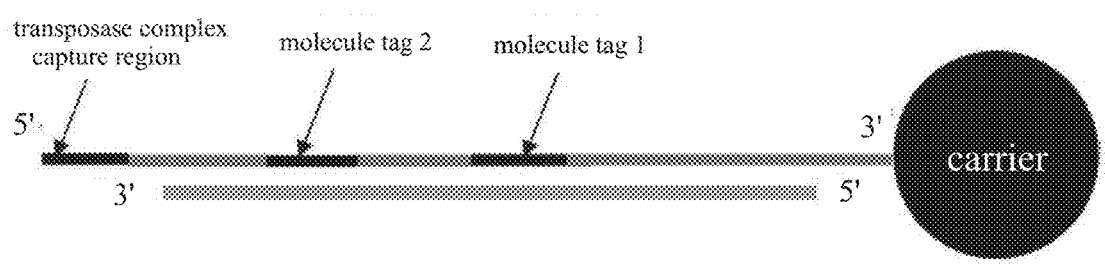
FIG. 2 is a schematic diagram of the structure of a molecule tag carrier.

A carrier with multiple copies of molecule tags (referred to as a molecule tag carrier for short) refers to multiple copies of oligonucleotides which have a same nucleotide sequence served as molecule tags are loaded on one carrier. In this step, various types of carriers with multiple copies of molecule tags were prepared according to a "dispersion-aggregation-dispersion" technique. A schematic structure of a molecule tag carrier is shown in FIG. 2.

1.1 Connection for a specific linker sequence to a carrier through the biotin-streptavidin interaction 1.1.1 Preparation of a specific linker sequence The specific linker sequence is called a linker. A linker is a double-stranded DNA molecule with both sticky ends. The linker was obtained by annealing a Linker-F solution in a concentration of 100 µM and a Linker-R solution in a concentration of 100 µM.

Linker-F is a single-stranded DNA molecule modified with double biotin groups at 3' end. Linker-F is of a nucleotide sequence as follows.

Linker-F (SEQ ID NO: 1 of the sequence listing):

```
5'-CTTCCGGCAGAACGACATGGCTACGAAAAAAAAAA-3'.
```

Linker-R is a single-stranded DNA molecule with a nucleotide sequence as follows.

Linker-R (SEQ ID NO: 2 of the sequence listing):

```
5'-CGTAGCCATGTCGTTCTGCC-3'.
```

1.1.2 Obtaining a carrier

The carrier is magnetic beads coupled with streptavidin, with a product name of Dynabeads M-280 streptation (Invitrogen) and an article number of 11206D, referred to as M280 magnetic beads in below.

1.1.3 The linker prepared in step 1.1.1 was connected to the M280 magnetic beads obtained in step 1.1.2 through the biotin-streptavidin interaction, thus obtaining magnetic beads with the linker.

The product obtained in step 1.1.3 is specifically in a form of magnetic bead suspension, thus it is called linker-magnetic bead suspension. In the linker-magnetic bead suspension, the linker was connected to the magnetic bead, in which the concentration of the linker is 1.6 µM and an average of 86,000 linkers were connected to each magnetic bead.

1.2 Four 384-well plates (with a total of 1536 wells) were taken, 2 µl 1-F solution (100 µM) and 2 µl 1-R solution (100 µM) were added into each well and then annealing to form a tag fragment 1.

1-F and 1-R are each a single-stranded DNA molecule with a nucleotide sequence as follows.

1-F (SEQ ID NO: 3 of the Sequence Listing):

```
5'-molecule tag 1-ACCCTGACTAGGTCGC-3';
```

1-R (SEQ ID NO: 4 of the Sequence Listing):

```
5'-GGAAGGCGACCTAGTCAGGGT-molecule tag 1'-
CGCAGA-3'.
```

The molecule tag 1 in this example consists of 10 nucleotides.

The molecule tag 1' and the molecule tag 1 are reverse complementary with each other.

The molecule tags 1 in different wells are individually different, thus a total of 1536 kinds of molecule tags 1 are presented in the 1536 wells.

1.3 2.5 µl of the linker-magnetic bead suspension prepared in step 1.1 was added to each well of the four 384-well plates obtained in step 1.2, and then T4 DNA ligase and the corresponding buffer were added and reacted at 25° C. for 1 hour.

1.4 After the completion of step 1.3, all the magnetic beads in the four 384-well plates were collected into a new centrifuge tube.

1.5 The magnetic beads obtained in step 1.4 were washed with the low-salt magnetic bead washing buffer, followed by resuspending with the working solution of ligation buffer to obtain a magnetic bead suspension with the linker in a concentration of 1.6 µM.

1.6 Four new 384-well plates (with a total of 1536 wells) were taken, 2 µl 2-F solution (100 µM) and 2 µl 2-R solution (100 µM) were added into each well and then annealing to form a tag fragment 2.

2-F and 2-R are each a single-stranded DNA with a nucleotide sequence as follows.

2-F (SEQ ID NO: 5 of the sequence listing):

```
5'-GCACTGACGACATGATCACCAAGGATCGATAGTCCATGCTAGG
CGTCGTTTTA-molecule tag 2-TCTGCG-3';
```

2-R (SEQ ID NO: 6 of the sequence listing):

```
5'-molecule tag 2'-TAAAACGACG-3'.
```

In 2-F, the transposase complex capture region is underlined.

The molecule tag 2 in this example consists of 10 nucleotides.

The molecule tag 2' and the molecule tag 2 are reverse complementary with each other.

The molecule tags 2 in different wells are individually different, thus a total of 1536 kinds of molecule tags 2 are presented in the 1536 wells.

1.7 2.5 µl of the magnetic bead suspension obtained in step 1.5 was added to each well of the four 384-well plates obtained in step 1.6, and then T4 DNA ligase and the corresponding buffer were added and reacted at 25° C. for 1 hour.

1.8 After the completion of step 1.7, all the magnetic beads in the four 384-well plates were collected into a new centrifuge tube.

1.9 The magnetic beads obtained in step 1.8 were fully washed with the low-salt magnetic bead washing buffer, followed by resuspending with the low-salt magnetic bead washing buffer to obtain a magnetic bead suspension with the linker in a concentration of 1.6 µM.

The magnetic bead suspension obtained in step 1.9 is named molecule tag carrier suspension.

The magnetic beads in the molecule tag carrier suspension are all connected to specific DNA molecules. The specific DNA molecule is a partially double-stranded structure composed of a first single-stranded DNA molecule and a second single-stranded DNA molecule. The first single-stranded DNA molecule consists of the following three regions in sequence from the 5'→3' direction: a 5' end region, a middle region and a 3' end region. The second single-stranded DNA molecule is entirely reverse complementary with the middle region of the first single-stranded DNA molecule to form the partially double-stranded structure. The 5' end region of the first single-stranded DNA molecule comprises a transposase complex capture region. The 3' end of the first single-stranded DNA molecule is connected to the surface of the magnetic bead through the biotin-streptavidin interaction. The middle region of the first single-stranded DNA molecule comprises the molecule tag 1 and the molecule tag 2.

In the preparation process as described above, 1536 kinds of molecule tags 1 and 1536 kinds of molecule tags 2 were introduced, and one specific molecule tag 1 and one specific molecule tag 2 were combined to form a specific molecule tag combination, thus magnetic beads which can carry 2,359,296 kinds of different molecule tag combinations were presented in the molecule tag carrier suspension, in which each magnetic bead is connected to a multiple of specific DNA molecules (belonging to a same kind) which contain one same kind of specific molecule tag.

2. Preparation of a cell tag carrier

Figure 3:
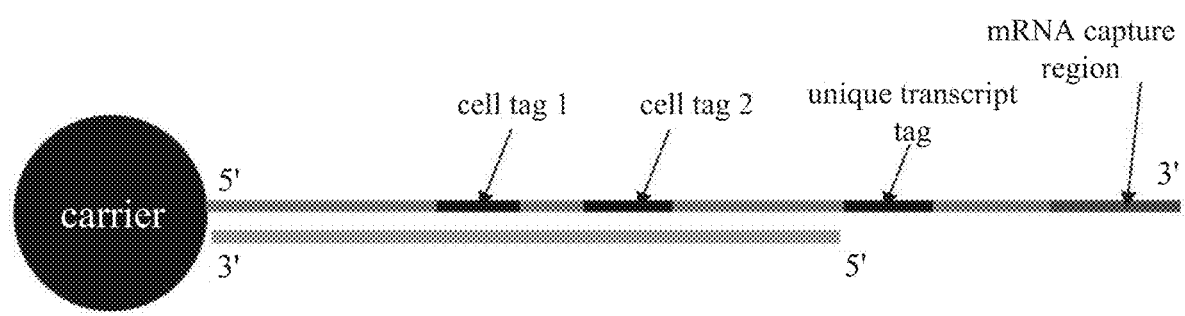
FIG. 3 is a schematic diagram of the structure of a cell tag carrier.

In this step, various types of carriers with multiple copies of cell tags (referred to as a cell tag carrier for short) were prepared according to a "dispersion-aggregation-dispersion" technique. A schematic structure of a cell tag carrier is shown in FIG. 3.

2.1 Preparation of a specific linker sequence

The specific linker sequence is called a linker. A linker is a double-stranded DNA molecule with both sticky ends. A linker solution was obtained by annealing a Linker-F solution in a concentration of 100 μM and a Linker-R solution in a concentration of 100 μM and then diluting with the TE buffer. The concentration of the linker in the linker solution is 33 μM.

Linker-F is a single-stranded DNA molecule modified with double biotin groups at 5'end. Linker-F is of a nucleotide sequence as follows.

Linker-F (SEQ ID NO: 7 of the sequence listing):

```
5'-iSp18-TTTTTCCCGTAGCCATGTCGTTCTGCG-3'.
```

Linker-R is a single-stranded DNA molecule with a nucleotide sequence as follows.

Linker-R (SEQ ID NO: 8 of the sequence listing):

```
5'-ACGACATGGCTACGGG-3'.
```

In the Linker-F, iSp18 represents a backbone formed by 18 carbon atoms.

2.2 Four 384-well plates (with a total of 1536 wells) were taken, 2 μl 3-F solution (100 μM) and 2 μl 3-R solution (100 μM) were added into each well and then annealing to form a tag fragment 3.

3-F and 3-R are each a single-stranded DNA molecule with a nucleotide sequence as follows.

3-F (SEQ ID NO: 9 of the sequence listing):

```
5'-cell tag 1-ACCTGAGATCGC-3';
```

3-R (SEQ ID NO: 10 of the sequence listing):

```
5'-GGAAGGGCGATCTCAGGT-cell tag 1'-CGCAGA-3'.
```

The cell tag 1 in this example consists of 10 nucleotides.

The cell tag 1' and the cell tag 1 are reverse complementary with each other.

The cell tags 1 in different wells are individually different, thus a total of 1536 kinds of cell tags 1 are presented in the 1536 wells.

2.3 0.781 μl of the linker solution prepared in step 2.1 was added to each well of the four 384-well plates obtained in step 2.2, and then T4 DNA ligase and the corresponding buffer were added and reacted at 25° C. for 1 hour.

2.4 Obtaining a carrier

The carrier is magnetic beads coupled with streptavidin, with a product name of Streptavidin Coated Polystyrene Particles (SVP-200-4, Spherotech), referred to as SVP-200-4 magnetic beads as below.

2.5 In the four 384-well plates obtained in step 2.3, the DNA molecules in each well were connected to the SVP-200-4 magnetic beads through the biotin-streptavidin interaction.

2.6 After the completion of step 2.5, all the magnetic beads in the four 384-well plates were collected into a new centrifuge tube.

2.7 The magnetic beads obtained in step 2.6 were washed with the low-salt magnetic bead washing buffer, followed by resuspending with the working solution of ligation buffer to obtain a magnetic bead suspension with the linker in a concentration of 10 μM. In the magnetic bead suspension, an average of 524,025,069 linkers were connected to each magnetic bead.

2.8 Four new 384-well plates (with a total of 1536 wells) were taken, 0.5 μl 4-F solution (100 μM) and 0.5 μl 4-R solution (100 μM) were added into each well and then annealing to form a tag fragment 4.

4-F and 4-R are each a single-stranded DNA molecule with a nucleotide sequence as follows.

4-F (SEQ ID NO: 11 of the Sequence Listing):

```
5'-CCTTCC-cell tag 2-CGATG-NNNNNNNNNN-TTTTTTTTTTTTTTTTTTTTV-3';
```

4-R (SEQ ID NO: 12 of the sequence listing):

```
5'-CATCG-cell tag 2'-3'.
```

In 4-F, V represents A, C or G, the box marks a unique transcript tag (unique molecular identifier, UMI), and the underlined wavy line indicates the mRNA capture region.

The cell tag 2 in this example consists of 10 nucleotides.

The cell tag 2' and the cell tag 2 are reverse complementary with each other.

The cell tags 2 in different wells are individually different, thus a total of 1536 kinds of cell tags 2 are presented in the 1536 wells.

The unique transcript tag in this example consists of 10 nucleotides (Ns), and each 4-F has one unique transcript tag.

2.9 5 μl of the magnetic bead suspension obtained in step 2.7 was added to each well of the four 384-well plates obtained in step 2.8, and then T4 DNA ligase and the corresponding buffer were added and reacted at 25° C. for 1 hour.

2.10 After the completion of step 2.9, all the magnetic beads in the four 384-well plates were collected into a new centrifuge tube.

2.11 The magnetic beads obtained in step 2.10 were fully washed with the low-salt magnetic bead washing buffer, followed by resuspending with the low-salt magnetic bead washing buffer to obtain a magnetic bead suspension.

The magnetic bead suspension obtained in step 2.11 is named cell tag carrier suspension.

In the cell tag carrier suspension, the concentration of magnetic beads is 4000/μl. The magnetic beads in the cell tag carrier suspension are all connected to specific DNA molecules. The specific DNA molecule in this example is a partially double-stranded structure composed of a third single-stranded DNA molecule and a fourth single-stranded DNA molecule. The third single-stranded DNA molecule consists of the following three regions in sequence from the 5'→3' direction: a 5' end region, a middle region and a 3' end region. The fourth single-stranded DNA molecule is entirely reverse complementary with the middle region of the third single-stranded DNA molecule to form the partially double-stranded structure. The 5' end of the third single-stranded DNA molecule is connected to the magnetic beads through the biotin-streptavidin interaction. The 3' end region of the third single-stranded DNA molecule comprises a unique transcript tag and an mRNA capture region in sequence from the 5'→3' direction. The middle region of the third single-stranded DNA molecule comprises the cell tag 1 and the cell tag 2.

In the preparation process as described above, 1536 kinds of cell tags 1 and 1536 kinds of cell tags 2 were introduced, and one specific cell tag 1 and one specific cell tag 2 were combined to form a specific cell tag combination, thus magnetic beads which can carry 2,359,296 kinds of different cell tag combinations were presented in the cell tag carrier suspension, in which each magnetic bead is connected to a multiple of specific DNA molecules (belonging to a same kind) which contain one same kind of specific cell tag, and in which each of the specific DNA molecules connecting to the magnetic bead has one kind of unique transcript tag, that is, the unique transcript tag comprised in each specific DNA molecule on each magnetic bead is different.

3. Preparation of a microwell chip and obtaining a full-length transcript amplification product 3.1 Preparation of the microwell chip 3.1.1 A microwell chip made of polydimethylsiloxane (PDMS) was prepared by using the micron structure array obtained by coating SU-8 photoresist on the surface of a silicon wafer as a mold. Each microwell chip has about 100,000 microwells and each microwell has a diameter of 25 μm and a height of 30 μm.

3.1.2 The microwell chip obtained in step 3.1.1 was subjected to plasma treatment on its surface to expose the hydroxyl group, thereby obtaining hydrophilicity to some extent.

3.1.3 The microwell chip obtained in step 3.1.2 was arranged into a 6-well plate, with one microwell chip per well.

3.1.4 3 ml of diethyl pyrocarbonate-treated water (DEPC water) was added to each well of the 6-well plate obtained in step 3.1.3, stilled for 30 minutes, and then discard the liquid in the wells.

3.1.5 3 ml of PBS buffer was added to each well of the 6-well plate obtained in step 3.1.4, and then discard the liquid in the wells.

3.1.6 3 ml of PBS buffer was again added to each well of the 6-well plate obtained in step 3.1.5, and then discard the liquid in the wells.

3.1.7 2.5 ml of PBS buffer was added to each well of the 6-well plate obtained in step 3.1.6.

The following steps 3.2, 3.3 and 3.4 are all exemplified through one microwell chip.

3.2 Addition of the cell tag carrier to the microwell chip 3.2.1 The magnetic beads in the cell tag carrier suspension prepared in step 2 were collected. About 400,000 magnetic beads collected were resuspended in 200 μl carrier loading buffer, and then uniformly loaded onto the surface of the microwell chip obtained in step 3.1, stilled at room temperature for 10 minutes. The liquid in the microwell chip was gently aspirated from one side of the microwell chip, and the magnetic beads therein were recovered. The magnetic beads recovered were resuspended in 200 μl carrier loading buffer, and then uniformly loaded onto the surface of the microwell chip, stilled at room temperature for 5 minutes.

3.2.2 After the completion of step 3.2.1, the liquid was gently aspirated from one side of the microwell chip, followed by washing the microwell chip twice with PBS buffer. Each washing process was performed by gently adding 3 ml of PBS buffer through the side and then aspirating the liquid from the side.

3.3 Addition of cells to the microwell chip 3.3.1 100,000 cells were fully suspended in 3 ml of PBS buffer, and then added into the microwell chip obtained in step 3.2 through the side of the chip, stilled for 30 minutes.

3.3.2 After the completion of step 3.3.1, the liquid was gently aspirated from the side of the microwell chip, followed by washing the microwell chip twice with PBS buffer. Each washing process was performed by gently adding 3 ml of PBS buffer through the side and then aspirating the liquid from the side.

3.4 Lysis of cells and capture of mRNAs 3.4.1 A polycarbonate filter membrane with a pore size of 0.01 μm was coated on the surface of the microwell chip obtained in step 3.3, and 3 ml of cell lysate was added, stilled at room temperature for 30 minutes.

3.4.2 After the completion of step 3.4.1, the liquid was gently aspirated from the side of the microwell chip, followed by washing the microwell chip twice with the washing buffer. Each washing process was performed by gently adding 3 ml of the washing buffer through the side and then aspirating the liquid from the side.

3.4.3 After the completion of step 3.4.2, the microwell chips were transferred to a new 6-well plate which had been added with 1 ml of washing buffer per well, and the surface of the microwell chip on which the microwells are existed faces down for collecting the magnetic beads.

In theory, one magnetic bead can capture all the mRNA molecules in one single cell and each mRNA molecule of the single cell is connected to a specific DNA molecule of the magnetic bead.

3.5 PCR amplification to obtain cDNAs with cell tags 3.5.1 All the magnetic beads obtained in step 3.4 were used to prepare a reverse transcription reaction system for the reverse transcription reaction.

Reverse transcription reaction system (20 μl): all magnetic beads, 2 μl dNTP (10 mM), 10 reverse transcriptase (200 U/μl), 0.5 μl RNaseOUT™ (40 U/μL), 4 μl 5× Superscript II first-strand buffer, 1 μl DTT solution (100 mM), 40 Betaine solution (5M), 60 $MgCl_2$ solution (25 mM), 0.2 μl TSO primer solution (100 μM), and water as the balance.

Superscript II first-strand buffer: 375 mM KCl, 15 mM $MgCl_2$, 250 mM Tris-HCl buffer as the solvent (pH 8.3).

TSO primer (SEQ ID NO: 13 of the sequence listing):

```
5'-CGTAGCCATGTCGTTCTGrGrG+G-3';
```

"r" represents the nucleotide after the "r" is a ribonucleotide, and "+" represents the nucleotide after the "+" is a locked nucleic acid (LNA).

Reaction condition for the reverse transcription reaction: 42° C., 90 minutes.

3.5.2 After the completion of step 3.5.1, the magnetic beads were collected and washed twice with the low-salt magnetic bead washing buffer for preparation of an exonuclease reaction system to be reacted.

Exonuclease reaction system (50 μl): all magnetic beads, 1 μl exonuclease (Exonuclease I, 20 U/μl), 5 μl 10× Exonuclease I Reaction Buffer, and water as the balance.

Reaction condition: 37° C., 10 minutes.

3.5.3 After the completion of step 3.5.2, the magnetic beads were collected and washed twice with the low-salt magnetic bead washing buffer for preparation of a PCR reaction system to be reacted.

PCR reaction system (100 μl): all magnetic beads, 50 μl 2×KAPA HiFi HotStart Ready Mix, 5 μl ISO primer solution (10 μM), and water as the balance.

ISO primer (SEQ ID NO: 14 of the sequence listing):

```
5'-CGTAGCCATGTCGTTCTG-3'.
```

PCR amplification condition: 98° C. for 3 minutes; 98° C. for 20 seconds, 67° C. for 15 seconds, 72° C. for 6 minutes (14 cycles); and 72° C. for 5 minutes.

3.5.4 After the completion of step 3.5.3, the magnetic beads were adsorbed with a magnet separator and the supernatant was collected, followed by purification through XP magnetic beads and collection of the purified product. The purified product is a full-length transcript amplification product.

There are a large number of cDNAs with cell tags in the full-length transcript amplification product. Each cDNA derived from one same single cell has a same cell tag, and the cDNAs derived from different single cells have different cell tags. The cDNAs derived from the same single cell each have a different transcript tag.

4. Preparation of a transposase complex and obtaining a sequencing library

Figure 5:
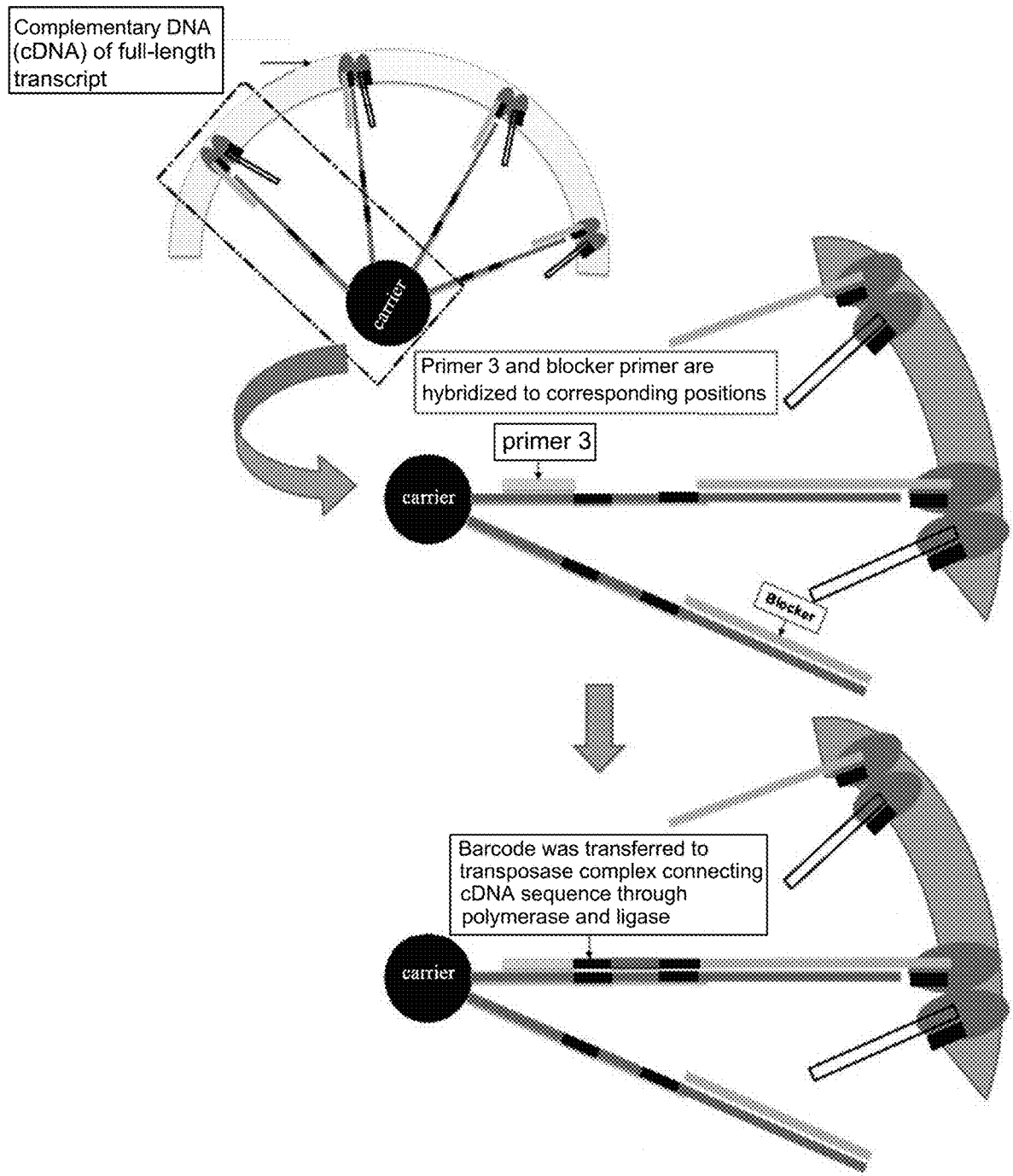
FIG. 5 is a schematic diagram of the principle and procedure of preparing a transposase complex and obtaining a sequencing library.
Figure 5:
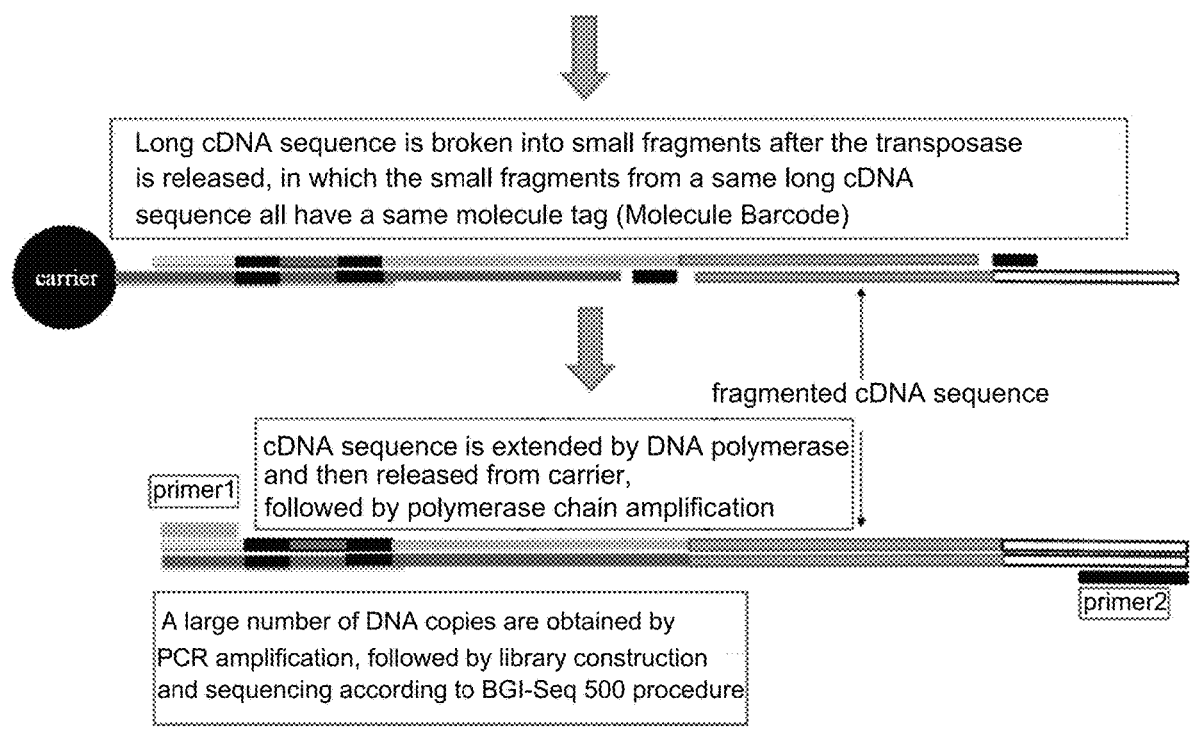

The schematic diagram of principle and procedure is shown in FIG. 5.

4.1 The transposon 1F and the transposon 1R were equimolarly mixed and annealed to obtain a transposon 1. The annealed product is in a form of solution, also known as transposon 1 solution, in which the concentration of the transposon 1 is 50 μM.

Transposon 1F and transposon 1R are each a single-stranded DNA molecule with a nucleotide sequence as follows.

Transposon 1F (SEQ ID NO: 15 of the sequence listing):

```
5'-CCTAGCATGGACTATCGATCCTTGGTGATCATGTCGTCAGTGCT
TGTCTTCCTAAGATGTGTATAAGAGACAG-3';
```

Transposon 1R (SEQ ID NO: 16 of the sequence listing):
5'-CTGTCTCTTATACACATCT-3'.

4.2 The transposon 2F and the transposon 2R were equimolarly mixed and annealed to obtain a transposon 2. The annealed product is in a form of solution, also known as transposon 2 solution, in which the concentration of the transposon 2 is 50 μM.

Transposon 2F and transposon 2R are each a single-stranded DNA molecule with a nucleotide sequence as below.

Transposon 2F (SEQ ID NO: 17 of the sequence listing):

```
5'-GAGACGTTCTCGACTCAGCAGAAGATGTGTATAAGAGACAG-3';
```

Transposon 2R (SEQ ID NO: 18 of the sequence listing):
5'-CTGTCTCTTATACACATCT-3'.

4.3 11.8 μl Tn5 transposase solution, 1.6 μl transposon 1 solution, 1.6 μl transposon 2 solution and 25 μl glycerol solution were mixed on ice and then reacted at 30° C. for 1 hour to obtain transposase complex solution, which was then diluted with a glycerol solution, thus obtaining transposase complex dilution, with the transposon 1 and the transposon 2 in a total concentration of 0.5 pmol/μl.

The concentration of Tn5 transposase in the Tn5 transposase solution is 1 U/μl.

The glycerin solution was obtained by diluting glycerin with the TE buffer, with the glycerin in a concentration of 50 g/100 ml.

4.4 The reaction system was prepared on ice and subjected to the transposition reaction to obtain a transposition product.

Reaction system (10 μl): 2 μl 5× transposase interruption buffer, the full-length transcript amplification product prepared in step 3 (DNA content of 2 ng), 1.5 μl transposase complex dilution obtained in step 4.3, and water as the balance.

5× transposase interruption buffer: 50% (by volume) dimethylformamide (DMF), 25 mM $MgCl_2$, and 50 mM HEPES-KOH buffer as a solvent (pH 8.5).

Reaction condition: 55° C., 10 minutes, immediately placed on ice after reaction.

Figure 4:
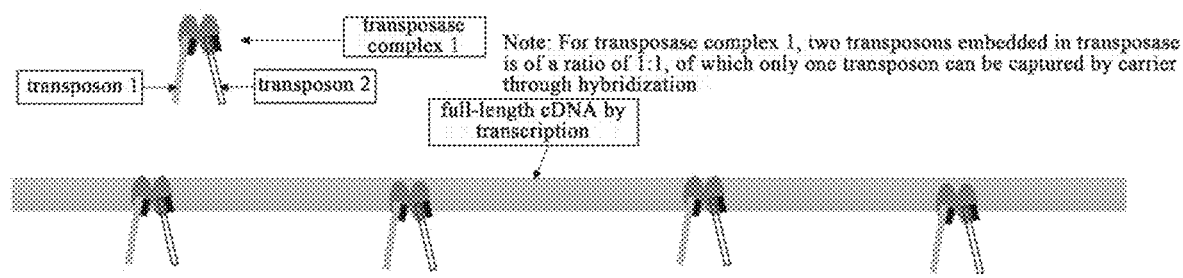
FIG. 4 is a schematic diagram of a transposition product.

The schematic diagram of the transposition product is shown in FIG. 4.

4.5 15 μl water and 25 μl 2× hybridization buffer were added to the system obtained in step 4.4 to obtain transposition product dilution.

2× hybridization buffer: 2000 mM NaCl, 0.1% (by volume) Tween-20, and 100 mM Tris-HCl buffer as a solvent (pH 7.5).

4.6 About 10 million magnetic beads were collected from the molecule tag carrier suspension prepared in step 1, washed with 50 μl low-salt magnetic bead washing buffer, then resuspended in 50 μl strong alkaline denaturing buffer and incubated at room temperature for 5 minutes, after that the magnetic beads were collected again, which were further washed with 50 μl strong alkaline denaturing buffer, 50 μl low-salt magnetic bead washing buffer and 50 μl hybridization buffer, and finally resuspended in 50 µl hybridization buffer to obtain a magnetic bead suspension.

Strong alkaline denaturing buffer: 1.6M KOH, 1 mM EDTA, and water as the balance.

Hybridization buffer: 1000 mM NaCl, 0.05% (by volume) Tween-20, and 50 mM Tris-HCl buffer as a solvent (pH 7.5).

4.7 50 µl of the transposition product dilution prepared in step 4.5 and 50 µl of the magnetic bead suspension prepared in step 4.6 were mixed, reacted at 60° C. for 1 minute, naturally cooled to the room temperature and then hybridized at 25° C. for 1 hour.

4.8 2 µl of 100 µM blocker 1 solution (Blocker 1) and 1 µl of 100 µM primer 3 solution were added into the reaction system obtained in step 4.7, reacted on a vertical mixer at 25° C. for 0.5 hours and then collect the magnetic beads, which were washed with the low-salt magnetic bead washing buffer and prepared to be a reaction system to be reacted.

Reaction system (50 µl): all magnetic beads, 6 µl DNA polymerase solution (T4 DNA Polymerase, 3 U/µl), 1 µl ligase solution (T7 DNA ligase, 3000 U/µl), 25 µl 2×T7 DNA ligase buffer, 0.5 µl 25 mM dNTP solution, 5 µl 10 mM ATP solution, and water as the balance.

Blocker 1 (SEQ ID NO: 19 of the sequence listing):

5'-CCTAGCATGGACTATCGATCCTTGGTGATCATGTCGTCAGTGC-3'.

Primer 3 (SEQ ID NO: 20 of the sequence listing):

5'-CGTAGCCATGTCGTTCTGCCGGAAGGGCGACCTAGTCAGGGT-3'.

The 3' end of the Blocker 1 is modified with a biotin group.

Reaction condition: 20° C., 0.5 hours.

4.9 5 µl 0.44 g/100 ml sodium dodecyl sulfate (SDS) aqueous solution was added to the reaction system obtained in step 4.8 and incubated at room temperature for 10 minutes to make the transposase denatured and released from DNA molecules, after that the magnetic beads were collected, which were washed with the high-salt magnetic bead washing buffer and then the low-salt magnetic bead washing buffer. The magnetic beads were collected again to prepare the reaction system to be reacted.

Reaction system (50 µl): all magnetic beads, 1 µl polymerase solution (Standard Taq polymerase, 5 U/ul), 5 µl 10× thermopol buffer, 0.8 µl dNTP solution (25 mM), and water as the balance.

Reaction condition: 72° C., 10 minutes.

4.10 After the completion of step 4.9, the magnetic beads were adsorbed with the magnet separator and the supernatant was collected.

4.11 The polymerase chain amplification (12 to 14 cycles) was performed in the presence of the supernatant obtained in step 4.10 as a template, and primer 1 and primer 2 by using the Novizan TD601 PCR kit according to the instructions, followed by purification with XP magnetic beads and collection of the purified product (i.e. the sequencing library solution). There are a large number of cDNA molecules with molecule tags in the sequencing library solution. All the cDNA fragments derived from one same cDNA molecule have a same molecule tag, and the cDNA fragments derived from different cDNA molecules have different molecule tags.

Primer 1 (SEQ ID NO: 21 of the sequence listing):

5'-CGTAGCCATGTCGTTCTG-3';

Primer 2 (SEQ ID NO: 22 of the sequence listing):

5'-GAGACGTTCTCGACTCAGCAGA-3'.

5. Determination and quantification of single-cell mRNA molecules 5.1 The sequencing library solution obtained in step 4 was subjected to a cyclization reaction according to the small DNA library construction procedure under the BGIseq-500 standard, and then high-throughput sequencing by the BGIseq-500 sequencer.

5.2 The original sequencing results obtained in step 5.1 were assembled according to molecule tags to obtain the sequence of each mRNA, after that all the mRNA molecules in each single cell were obtained according to cell tags. Then, each mRNA molecule in each single cell was individually quantified according to the sequence count having different transcript tags and a same mRNA sequence.

Example 2 Specific Experiments Through the Method Established in Example 1

The cells are immortalized B lymphocytes.

Sequencing library solution was obtained according to the method established in Example 1.

Figure 6:
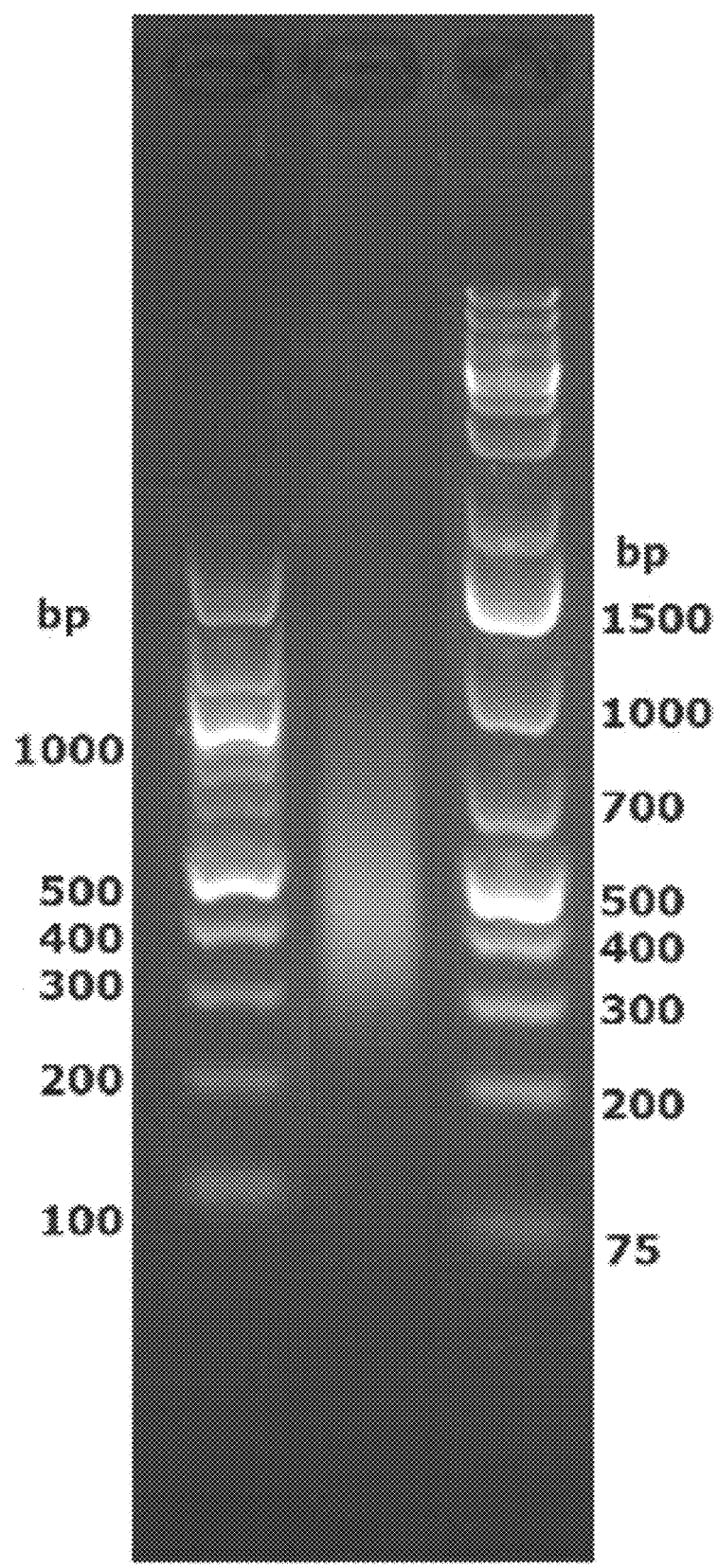
FIG. 6 is a picture of 1.5% agarose gel electrophoresis of sequencing library solution.

The 1.5% agarose gel electropherogram of the sequencing library solution is shown in FIG. 6.

In FIG. 6, the DNA Marker on the left is NEB 100 bp ladder, and the DNA Marker on the right is Thermofisher 1 kb plus DNA ladder. In the sequencing library solution, the band size is between 300-1000 bp, and the main band is about 450 bp.

The DNA content of the sequencing library solution is 222 ng, corresponding to 747.5 fmol (222/660/450*1000*1000) according to the conversion between the DNA content and the molar weight, which meets the requirement of standard cyclization reaction.

After the cyclization reaction, 13 ng (87 fmol) of single-stranded circular DNAs were obtained, which meets the requirement of sequencing.

The single-stranded circular DNAs were sequenced on the BGISEQ-500 sequencing platform based on the pair-end 100 bp, plus the single-end 54 bp and the single-end 53 bp. The pair-end 100 bp refers to the cDNA sequences contained in the sequencing library are sequenced 100 bp from both the 5' end and the 3' end. The single-end 54 bp is directed to the sequencing of molecule tags. The single-end 53 bp is directed to the sequencing of cell tags and unique transcript tags (UMIs).

Figure 7:
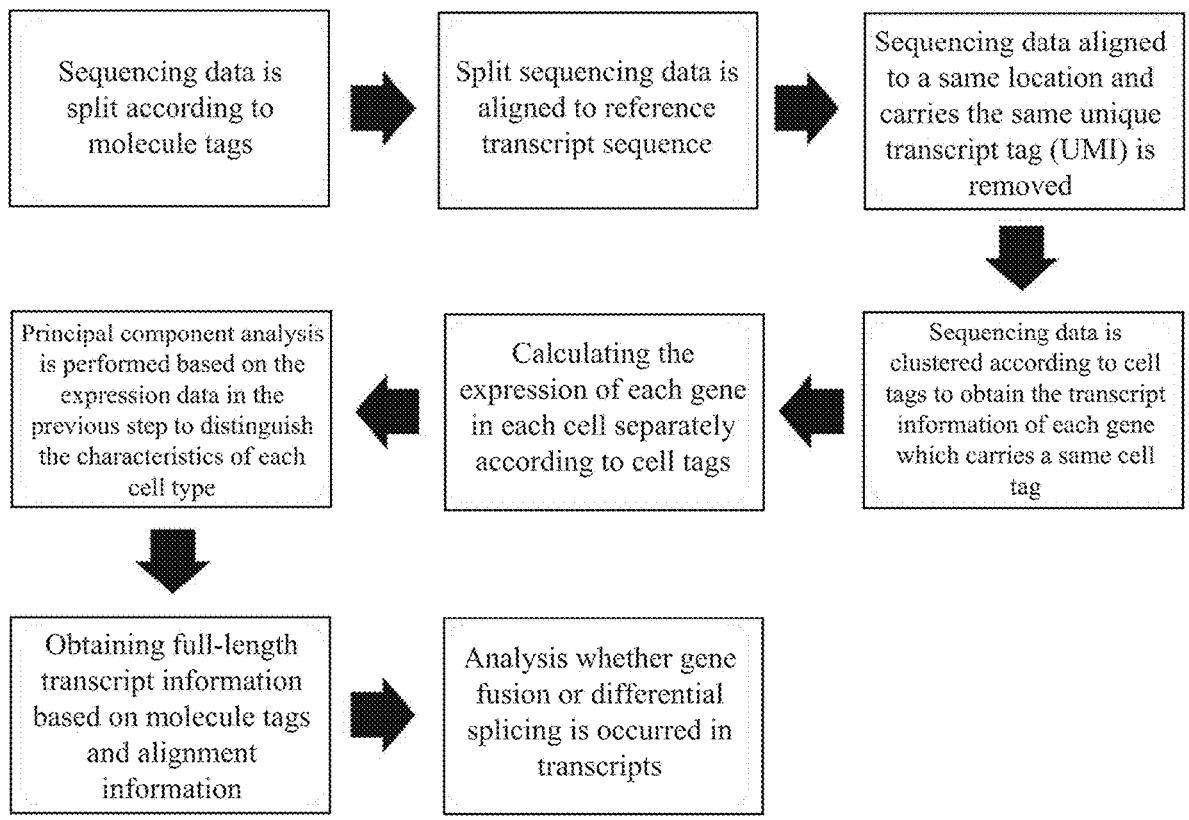
FIG. 7 is a flow chart of analysis and assembly of sequencing results.

The original sequencing results obtained were assembled according to molecule tags to obtain the sequence of each mRNA, after that mRNA molecules in each single cell were individually obtained according to cell tags. Then, each mRNA molecule in each single cell was individually quantified according to the sequence count having different transcript tags and a same mRNA sequence. The flow chart of analysis and assembly of sequencing results is shown in FIG. 7.

Figure 8:
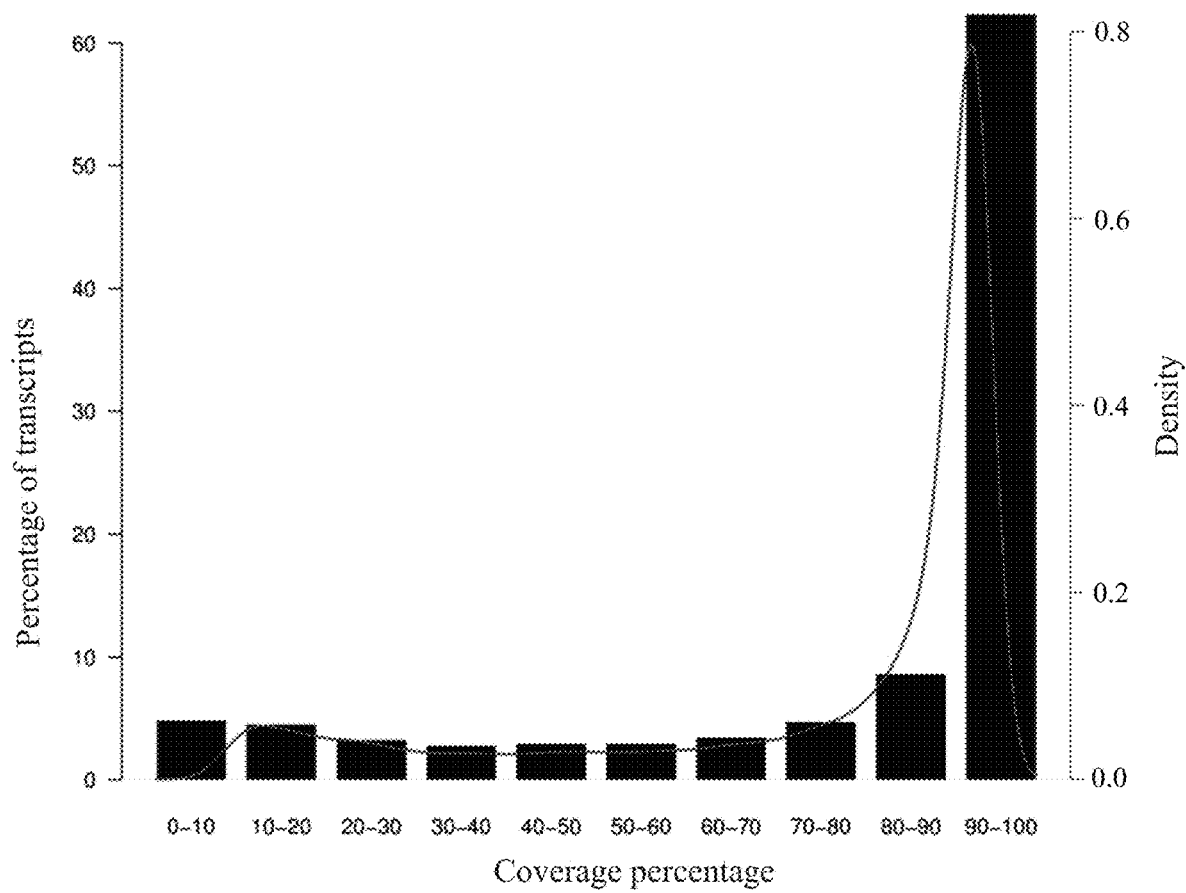
FIG. 8 is a graph of reads coverage of transcripts, where the X axis represents the reads coverage on transcript, the left Y axis represents the percentage of transcripts, and the right Y axis represents the density of transcripts.
Figure 9:
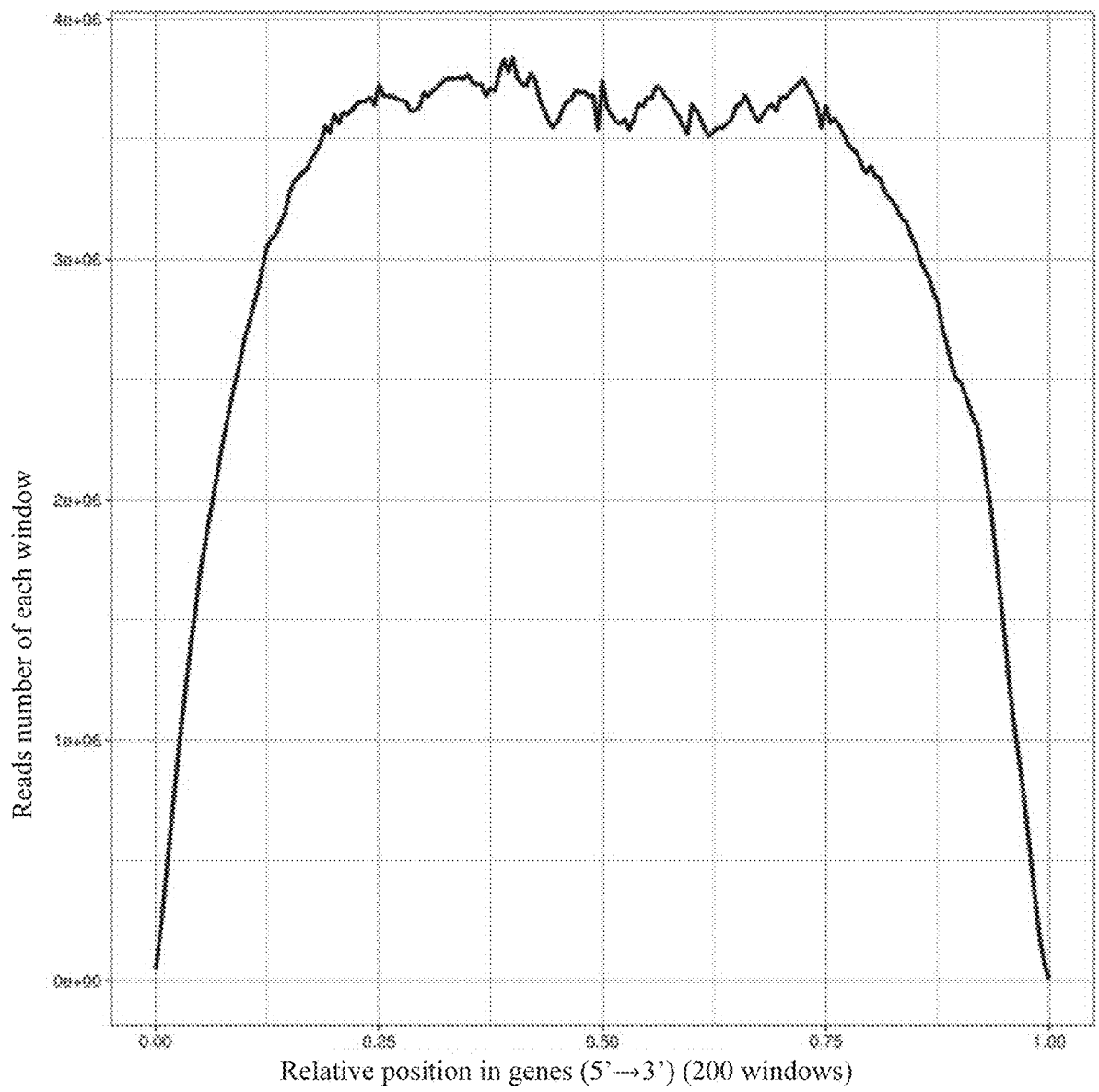
FIG. 9 is a graph of the distribution of reads on transcripts, where the X axis represents the relative position of transcripts, and the Y axis represents the reads number.

The reads were aligned to the refMrna.fa reference transcript sequence through the bowtie2 software, and the transcript coverage was counted, in which about 60% of the reference transcript sequence can be completely covered (as shown in FIG. 8) and reads are uniformly distributed on the reference transcript sequence (as shown in FIG. 9).

Figure 10:
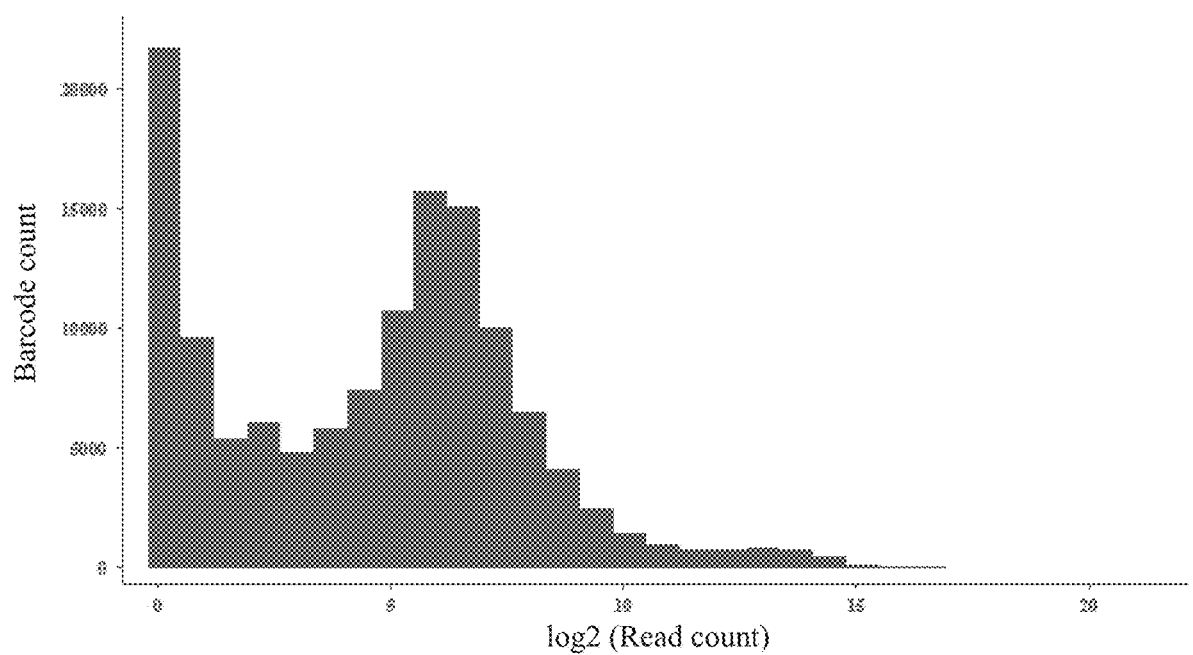
FIG. 10 is a graph of the reads distribution in each Barcode.

The reads that were not aligned to the genome were used for the analysis of single-cell barcode information. About 1.96% of the reads can be split into the single cell barcode. The reads distribution under each barcode is shown in FIG. 10. The average reads count under each barcode is 64 to 128.

Example 3

This example is similar to the example 1 except for some details in steps 1.2, 1.6, 2.2, 2.8 and 3.5. Therefore, only the differences are described as below.

Regarding the step 1.2, the four 384-well plates in example 1 were replaced with two 384-well plates in this example. Regarding the step 1.6, the four 384-well plates in example 1 were replaced with one 384-well plates in this example. In the preparation process of this example, 768 kinds of molecule tags 1 and 384 kinds of molecule tags 2 were introduced, one specific molecule tag 1 and one specific molecule tag 2 were combined to form a specific molecule tag combination, thus magnetic beads which can carry 294,912 kinds of different molecule tag combinations were presented in the molecule tag carrier suspension, in which each magnetic bead is connected to a multiple of specific DNA molecules (belonging to a same kind) which contain one same kind of specific molecule tag.

Regarding the step 2.2, the four 384-well plates in example 1 were replaced with two 384-well plates in this example. Regarding the step 2.8, the four 384-well plates in example 1 were replaced with one 384-well plates in this example. In the preparation process of this example, 768 kinds of cell tags 1 and 384 kinds of cell tags 2 were introduced, one specific cell tag 1 and one specific cell tag 2 were combined to form a specific cell tag combination, thus magnetic beads which can carry 294,912 kinds of different cell tag combinations were presented in the cell tag carrier suspension, in which each magnetic bead is connected to a multiple of specific DNA molecules (belonging to a same kind) which contain one same kind of specific cell tag, and in which each of the specific DNA molecules connecting to the magnetic bead has one kind of unique transcript tag, that is, the unique transcript tag comprised in each specific DNA molecule on each magnetic bead is different.

The step 3.5 in this example is rolling circle amplification to obtain cDNAs with cell tags, including steps 3.5.1 and 3.5.2 as below.

3.5.1 Double-stranded circular cDNAs were subjected to rolling circle amplification to obtain cDNAs with cell tags.

3.5.1.1 All the magnetic beads obtained in step 3.4 were used to prepare a reverse transcription reaction system for the reverse transcription reaction.

This step is same as the step 3.5.1 in the example 1.

3.5.1.2 After the completion of step 3.5.1.1, the magnetic beads were collected and washed twice with the low-salt magnetic bead washing buffer for preparation of an exonuclease reaction system to be reacted.

Exonuclease reaction system (50 µl): all magnetic beads, 10 exonuclease (Exonuclease I, 20 U/µl), 50 10× Exonuclease I Reaction Buffer, and water as the balance.

Reaction condition: 37° C., 10 minutes.

3.5.1.3 After the completion of step 3.5.1.2, the magnetic beads were collected and washed twice with the low-salt magnetic bead washing buffer for a PCR reaction system, that is, a full-length transcript amplification reaction.

PCR reaction system (100 µl): all magnetic beads, 50 µl 2×KAPA HiFi HotStart Ready Mix, 5 µl ISO primer solution (10 µM), and water as the balance.

ISO primer (SEQ ID NO: 23 of the sequence listing):

5'-AAGCdUdUCGTAGCCATGTCGTTCTG-3'.

PCR amplification condition: 98° C. for 3 minutes; 98° C. for 20 seconds, 67° C. for 15 seconds, 72° C. for 6 minutes, 14 cycles (the amplification cycle number is related to the cell addition amount); 72° C. for 5 minutes.

3.5.1.4 After the completion of step 3.5.1.3, the magnetic beads were adsorbed with a magnet separator and the supernatant was collected, followed by purification via 100 µL XP magnetic beads (Agencourt AMPure XP-Medium, A63882, AGENCOURT) according to the standard official procedure. The purified product is a full-length transcript amplification product.

3.5.1.5 1 µL USER enzyme (1 U/µL NEB) and 3 µL 10×stTaq Buffer (in a concentration of 10 times of standard Taq buffer, 100 mM Tris-HCl, 500 mM KCl, 15 mM MgCl$_2$) was added to the supernatant obtained in step 3.5.1.4 and the volume was made up to 30 µL with water, followed by reaction at 37° C. for 1 hour.

3.5.1.6 After the completion of step 3.5.1.5, the reaction tube was immediately taken out, 5 µL 10×TA Buffer was added and the volume was made up to 50 µL with water, followed by reaction at 70° C. for 30 minutes and then in a water bath at room temperature for 20 minutes.

3.5.1.7 After the completion of step 3.5.1.6, 2.75 µL 20× Circ Mix (10×TA Buffer, 0.1M ATP) and 0.1 µL T4 DNA ligase (Enzymatics, 600 U/µL) were added and the volume was made up to 55 µL with water, followed by reaction at room temperature for 2 hours.

3.5.1.8 After the completion of step 3.5.1.7, 55 µL XP magnetic beads (Agencourt AMPure XP-Medium, A63882, AGENCOURT) were added to the reaction system for purification according to the standard official procedure.

3.5.1.9 After the completion of step 3.5.1.8, 3 µL 10× Plasmid-safe Buffer, 3.38 µL Plasmid-Safe ATP-Dependent DNase (10 U/µL, Epicentre) and 1.2 µL 25 mM ATP were added and the volume was made up to 30 µL with water, followed by reaction at 37° C. for 1.5 hours.

10× Plasmid-safe Buffer (in a concentration of 10 times of linear DNA digestion buffer): 330 mM Tris-acetate (Tris-acetic acid, pH 7.5), 660 mM potassium acetate (potassium acetate), 100 mM magnesium acetate (magnesium acetate), 5.0 mM DTT.

3.5.1.10 After the completion of step 3.5.1.9, 30 µL XP magnetic beads (Agencourt AMPure XP-Medium, A63882, AGENCOURT) were added to the reaction system for purification according to the standard official procedure, after that the cyclization of double-stranded full-length transcripts was completed.

3.5.1.11 20 µL reaction solution for rolling circle amplification was added to the reaction product obtained in step 3.5.1.10 and the volume was made up to 40 µL with water.

Condition for rolling circle amplification: 95° C. for 1 minute, 65° C. for 1 minute, and 40° C. for 1 minute.

After the completion of rolling circle amplification, the reaction product was immediately placed on ice.

Reaction solution for rolling circle amplification was prepared by adding 40 µL 10×phi29 buffer (in a concentration of 10 times of phi29 buffer) to 4 µL Oligo (50 µM) for rolling circle amplification and making up the volume to 200 µL with water.

Oligo for rolling circle amplification (SEQ ID NO: 24 of the sequence listing):

5'-TTTTTTTTTTTTTTTT-3'.

3.5.1.12 44 μL of phi29 DNA polymerase reaction mixture was added to the reaction product obtained in step 3.5.1.11, followed by reaction at 30° C. for 10 minutes and then at 65° C. for 10 minutes.

3.5.1.13 After the completion of step 3.5.1.12, 5 μL 10×NEB buffer 2 (in a concentration of 10 times of NEB buffer 2), 0.4 μL dNTP Mix (25 mM for each dNTP), 0.5 μL ATP (0.1 M) and 0.5 μL primer for double-strand synthesis (10 μM) were added into the liquid containing 100 ng DNA obtained in step 3.5.1.12, and then placed in the PCR instrument for reaction according to conditions: 95° C. for 3 minutes, 58° C. for 30 seconds, with the reaction product taken out immediately after the reaction. After that, 2 μL DNA polymerase 1 (NEB, 5 U/μL) and 1 μL T4 DNA ligase (Enzymatics, 600 U/μL) were added and placed in the PCR instrument again for reaction according to conditions: 37° C. for 30 minutes, 75° C. for 20 minutes.

Primer for double-strand synthesis (SEQ ID NO: 21 of the sequence listing):

5'-CGTAGCCATGTCGTTCTG-3'.

3.5.1.14 After the completion of step 3.5.1.13, 50 μL XP magnetic beads (Agencourt AMPure XP-Medium, A63882, AGENCOURT) were added to the reaction system for purification according to the standard official procedure, after that the preparation and enrichment of mRNA full-length transcripts (i.e. cDNAs) was completed.

Figure 11:
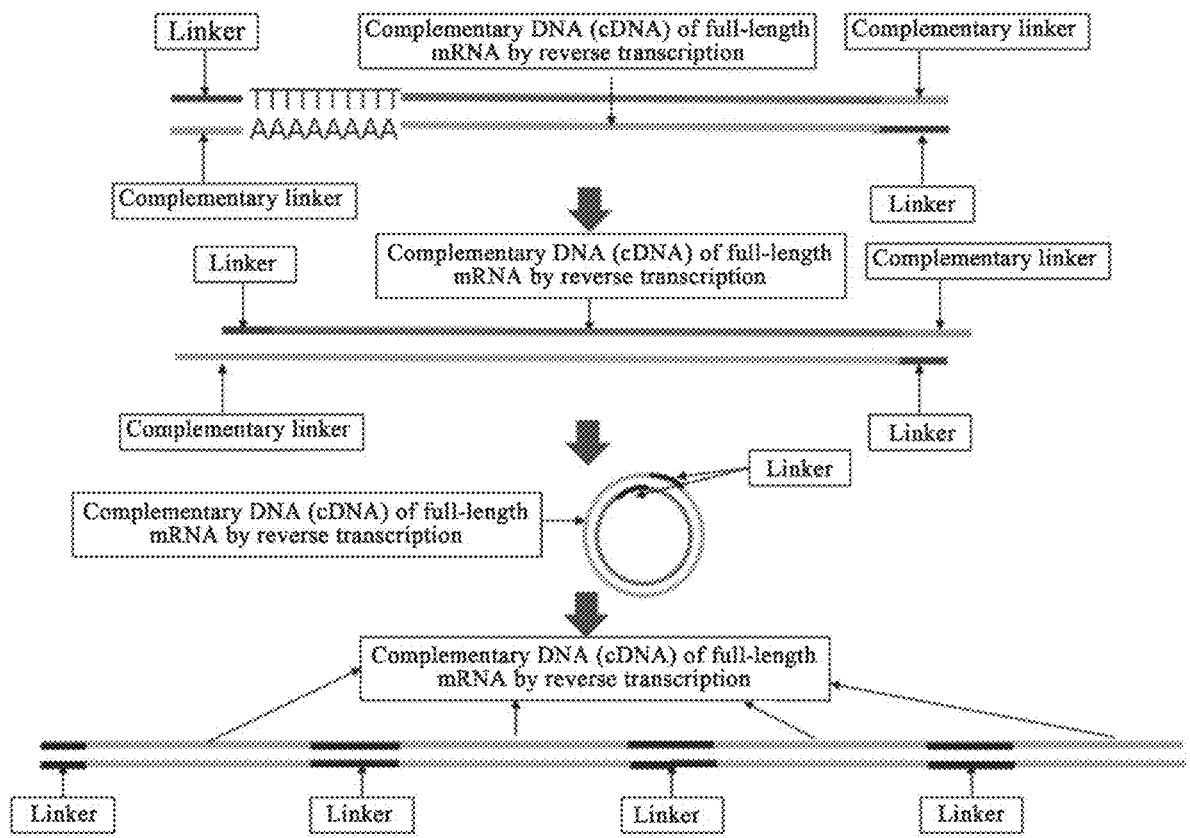
FIG. 11 is a flow chart of rolling circle amplification of circularized double strands to obtain cDNAs with cell tags.

The flow chart is shown in FIG. 11.

3.5.2 Single-stranded circular cDNAs were subjected to rolling circle amplification to obtain cDNAs with cell tags.

3.5.2.1 All the magnetic beads obtained in step 3.4 were used to prepare a reverse transcription reaction system for the reverse transcription reaction.

Reverse transcription reaction system (20 μl): all magnetic beads, 2 μl dNTP (10 mM), 1 μl reverse transcriptase (200 U/μl), 0.5 μl RNaseOUT™ (40 U/μL), 4 μl 5× Superscript II first-strand buffer, 1 μl DTT Solution (100 mM), 40 Betaine solution (5M), 6 μl MgCl$_2$ solution (25 mM), 0.2 μl TSO primer solution (200 μM), and water as the balance.

Superscript II first-strand buffer: 375 mM KCl, 15 mM MgCl$_2$, 250 mM Tris-HCl buffer as the solvent (pH 8.3).

TSO primer (SEQ ID NO: 25 of the sequence listing):

5'-GGAAACAGCTATGACCATGCGTAGCCATGTCGTTCTGrGrG3'.

"r" represents the nucleotide after the "r" is a ribonucleotide, and "+" represents the nucleotide after the "+" is a locked nucleic acid (LNA).

Reaction conditions for reverse transcription: 42° C., 90 minutes.

3.5.2.2 After the completion of step 3.5.2.1, the magnetic beads were collected and washed twice with the low-salt magnetic bead washing buffer for an exonuclease reaction system to be reacted.

Exonuclease reaction system (50 μl): all magnetic beads, 10 exonuclease (Exonuclease I, 20 U/μl), 5 μl 10× Exonuclease I Reaction Buffer, and water as the balance.

Reaction condition: 37° C., 10 minutes.

3.5.2.3 After the completion of step 3.5.2.2, the magnetic beads were collected and washed twice with the low-salt magnetic bead washing buffer for a PCR reaction, that is, a full-length transcript amplification reaction.

PCR reaction system (100 μl): all magnetic beads, 50 μl 2×KAPA HiFi HotStart Ready Mix, 5 μl ISO primer solution (10 μM), and water as the balance.

ISO primer (SEQ ID NO: 26 of the sequence listing):

5'phos-CGTAGCCATGTCGTTCTG-3'.

"5' phos" represents a phosphorylation modification at the 5'end.

PCR amplification condition: 98° C. for 3 minutes; 98° C. for 20 seconds, 67° C. for 15 seconds and 72° C. for 6 minutes for 5 cycles. After that, 5 μl of another PCR primer (10 μM) was added, and then reacted for another 10 cycles.

A cDNA amplification product with a linker at both ends was obtained.

Another PCR primer (SEQ ID NO: 27 of the sequence listing):

5'-GGAAACAGCTATGACCATG-3'.

3.5.2.4 After the completion of step 3.5.2.3, the magnetic beads were adsorbed with a magnet separator and the supernatant was collected, followed by purification through 100 μL XP magnetic beads (Agencourt AMPure XP-Medium, A63882, AGENCOURT) according to the standard official procedure.

3.5.2.5 The supernatant obtained in step 3.5.2.4 was subjected to single-strand cyclization reaction.

The cyclization reaction of single-stranded DNAs was conducted through the BGI library construction kit according to the operating instructions.

Oligo for single-strand cyclization reaction (SEQ ID NO: 28 of the sequence listing):

5'-GACATGGCTACGGGAAACAGCTAT-3'.

3.5.2.6 20 μL of reaction solution for rolling circle amplification was added to the reaction product obtained in step 3.5.2.5 and the volume was made up to 40 μL with water. The reaction condition for rolling circle amplification: 95° C. for 1 minute, 65° C. for 1 minute, and 40° C. for 1 minute. After the completion of the reaction, the reaction product was immediately taken out and placed on ice.

Reaction solution for rolling circle amplification was prepared by adding 40 μL 10×phi29 buffer (in a concentration of 10 times of phi29 buffer) into 4 μL of Oligo (50 μM) for rolling circle amplification, and making up to 200 μL with water.

Primer Oligo (SEQ ID NO: 27 of the sequence listing) for rolling circle amplification:

5'-GGAAACAGCTATGACCATG-3'.

3.5.2.7 44 μL of phi29 DNA polymerase reaction mixture was added to the reaction product obtained in step 3.5.2.6, followed by reaction at 30° C. for 10 minutes and then at 65° C. for 10 minutes.

3.5.2.8 After the completion of step 3.5.2.7, 5 μL 10×NEB buffer 2 (in a concentration of 10 times of NEB buffer 2), 0.4 μL dNTP Mix (25 mM for each dNTP), 0.5 μL ATP (0.1 M) and 0.5 μL primer for double-strand synthesis (10 μM) were added into the liquid containing 100 ng DNA obtained in step 3.5.2.7, and then placed in the PCR instrument for reaction according to conditions: 95° C. for 3 minutes, 58° C. for 30 seconds, with the reaction product taken out immediately after the reaction. After that, 2 μL DNA polymerase 1 (NEB, 5 U/μL) and 1 μL T4 DNA ligase (Enzymatics, 600 U/μL) were added and placed in the PCR instrument again for reaction according to conditions: 37° C. for 30 minutes, 75° C. for 20 minutes.

Primer for double-strand synthesis (SEQ ID NO: 21 of the sequence listing):

5'-CGTAGCCATGTCGTTCTG-3'.

3.5.2.9 After the completion of step 3.5.2.8, 50 μL XP magnetic beads (Agencourt AMPure XP-Medium, A63882, AGENCOURT) were added to the reaction system for purification according to the standard official procedure, after that the preparation and enrichment of mRNA full-length transcripts (i.e. cDNAs) was completed.

Figure 12:
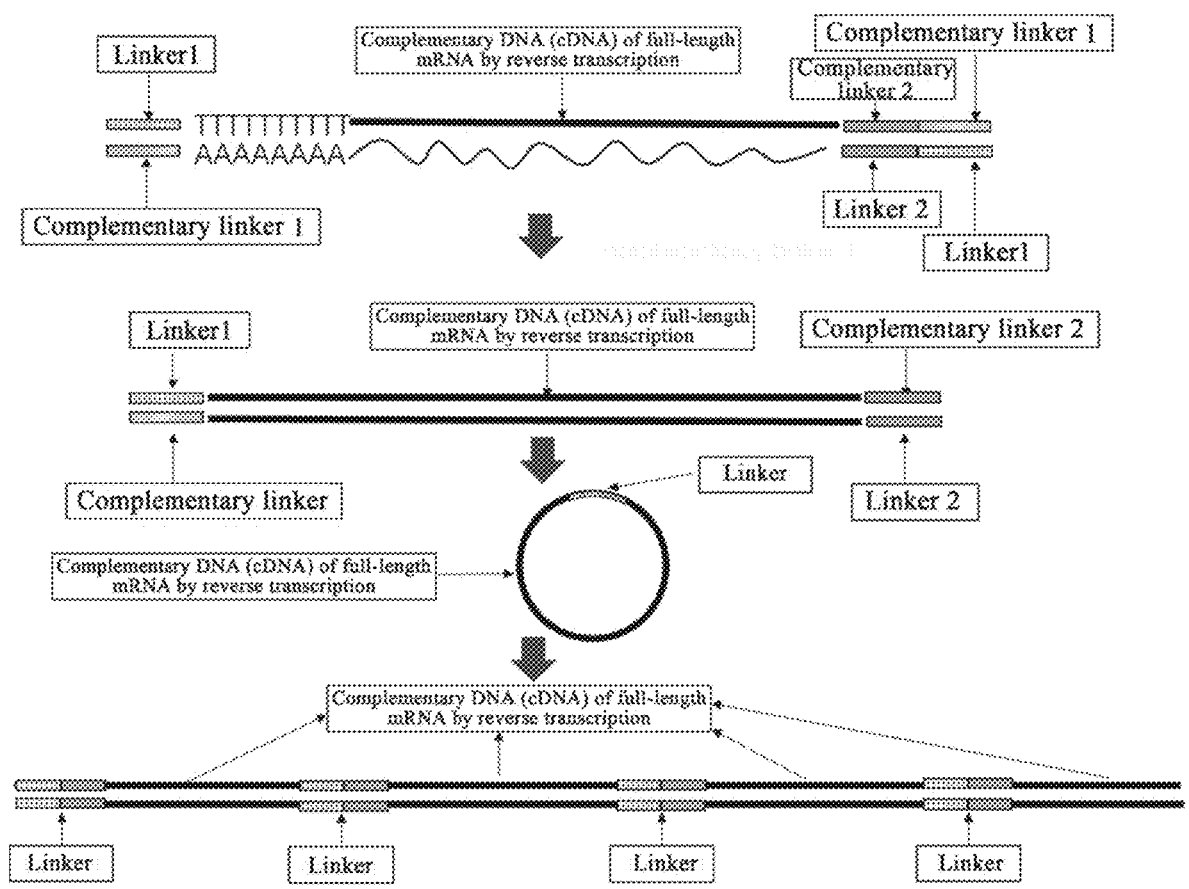
FIG. 12 is a flow chart of rolling circle amplification of circularized single strand to obtain cDNAs with cell tags.

The flow chart is shown in FIG. 12.

Example 4 Specific Experiments Through the Method Established in Example 3

The cells are immortalized B lymphocytes.

Sequencing library solution was obtained according to the method established in Example 3.

The reads were aligned to the refMrna.fa reference transcript sequence through the bowtie2 software, and the transcript coverage was analyzed, in which about 60% of the reference transcript sequence can be completely covered and reads are uniformly distributed on the reference transcript sequence.

The reads that were not aligned to the genome were used for the analysis of single-cell barcode information. About 1.96% of the reads can be split into the single cell barcode. The reads distribution under each barcode is shown in FIG. 10. The average reads number under each barcode is 64 to 128.

INDUSTRIAL APPLICATIONS

The present disclosure has the following advantages compared to the prior art.

(1) The present disclosure provides a solution for high-throughput sequencing of mRNA full-length transcripts, successfully solving the problem in the existing technology of either low throughput or unable to detect the full length of transcript despite high-throughput.
(2) The present disclosure uses a microwell chip instead of a microfluidic chip for single-cell separation, without a complicated control equipment such as a peristaltic pump or a syringe pump.
(3) The sequencing data generated by the library constructed in the present disclosure can be useful in de novo assembly of single-cell transcripts.

What is claimed is:

1. A method for obtaining full-length sequences of mRNA molecules of a single cell, comprising the steps of:
   (a) utilizing a carrier with a cell tag to capture mRNA molecules of the single cell, followed by performing a reverse transcription reaction to obtain cDNA molecules with cell tags,
   (b) utilizing a transposase complex and a carrier with a molecule tag to obtain cDNA fragments with molecule tags based on a virtual compartment, wherein the transposase complex inserts to the cDNA randomly, and then the cDNA inserted with the transposase complex is captured by the carrier with molecule tags forming one virtual compartment, to add the molecule tags to the cDNA;
   (c) high-throughput sequencing the cDNA fragments with the molecule tags obtained in step (b); and
   (d) assembling sequencing results obtained in step (c) to obtain full-length sequence of each mRNA molecule according to the molecule tag and obtaining full-length sequences of all the mRNA molecules in each single cell according to the cell tag,
   wherein the carrier with a cell tag is a solid carrier carrying the cell tag,
   the carrier with a molecule tag is a solid carrier carrying the molecule tag,
   each cDNA molecule derived from one single cell has a same cell tag and the cDNA molecules derived from different single cells have different cell tags, and
   all the cDNA fragments derived from one same cDNA molecule have a same molecule tag and the cDNA fragments derived from different cDNA molecules have different molecule tags.

2. The method according to claim 1, further comprising connecting a multiple of DNA molecules II to the surface of the solid carrier to obtain the carrier with a cell tag,
   wherein the DNA molecule II is a partially double-stranded structure composed of a third single-stranded DNA molecule and a fourth single-stranded DNA molecule, and
   the DNA molecule II comprises the cell tag and an mRNA capture region.

3. The method according to claim 2, wherein the third single-stranded DNA molecule consists of the following three regions in sequence from the 5' →3' direction: a 5' end region, a middle region and a 3' end region;
   the fourth single-stranded DNA molecule is entirely reverse complementary with the middle region of the third single-stranded DNA molecule to form the partially double-stranded structure.

4. The method according to claim 3, wherein
   the 5' end of the third single-stranded DNA molecule is connected to the surface of the solid carrier of the carrier with a cell tag,
   the 3' end region of the third single-stranded DNA molecule comprises the mRNA capture region,
   the middle region of the third single-stranded DNA molecule comprises the cell tag.

5. The method according to claim 2, wherein the mRNA molecules of the single cell are further quantified by a step of:
   quantifying each mRNA molecule in each single cell according to a sequence count of sequences having different unique transcript tags and a same mRNA sequence,
   wherein the carrier with a cell tag further contains a unique transcript tag, the cDNA molecules obtained in step (a) comprise the cell tags and the unique transcript tags, and
the cDNA molecules derived from the same single cell each have a different unique transcript tag.

6. The method according to claim 5, wherein
the unique transcript tag and the mRNA capture region are comprised in a 3' end region of the third single-stranded DNA molecule,
wherein the unique transcript tag consists of 8 to 50 nucleotides.

7. The method according to claim 2, wherein
the DNA molecules II connected to the surface of the solid carrier of each carrier with a cell tag belong to one same type which has a same nucleotide sequence.

8. The method according to claim 7, wherein
the surface of the solid carrier of each carrier with a cell tag is connected to 10,000,000 or more DNA molecules II belonging to the same type.

9. The method according to claim 1, further comprising connecting a multiple of DNA molecules I to the surface of the solid carrier to obtain the carrier with the molecule tag,
wherein the DNA molecule I is a partially double-stranded structure composed of a first single-stranded DNA molecule and a second single-stranded DNA molecule, and
the DNA molecule I comprises the molecule tag and a transposase complex capture region.

10. The method according to claim 9, wherein
a 3' end of the first single-stranded DNA molecule is connected to the surface of the solid carrier of the carrier with a molecule tag,
a 5' end region of the first single-stranded DNA molecule comprises a transposase complex capture region,
the middle region of the first single-stranded DNA molecule comprises a molecule tag.

11. The method according to claim 9, wherein
the transposase complex consists of a transposon 1, a transposon 2 and a transposase,
the transposon 1 is captured by the transposase complex capture region, and the transposon 2 is not captured by the transposase complex capture region.

12. The method according to claim 9, wherein
the DNA molecules I connected to the surface of the solid carrier of each carrier with a molecule tag belong to one same type which has a same nucleotide sequence.

13. The method according to claim 12, wherein
the surface of the solid carrier of each carrier with a molecule tag is connected to 10,000 or more DNA molecules I belonging to the same type.

14. The method according to claim 1, wherein the step of utilizing a carrier with a cell tag to capture mRNA molecules of the single cell is performed in a microwell chip or a microfluidic droplet system.

15. The method according to claim 1, wherein the method further comprises a step of enriching the cDNA molecules with the cell tags between step (a) and step (b), and/or
the method further comprises a step of enriching the cDNA fragments with the molecule tags between step (b) and step (c).

16. The method according to claim 15, wherein the step of enriching the cDNA molecules with the cell tags between step (a) and step (b) is a PCR amplification reaction or a rolling circle amplification.

17. The method according to claim 1, wherein
the carrier with a cell tag has one or more sets of cell tags to increase the cell type which can be tagged by the cell tag,
the carrier with a molecule tag has one or more sets of molecule tags to increase the molecule type which can be tagged by the molecule tag.

18. The method according to claim 1, wherein
the cell tag consists of 4 to 50 nucleotides, and the molecule tag consists of 4 to 50 nucleotides.

19. The method according to claim 1, wherein the solid carrier carrying the cell tag is magnetic beads, colloidal beads, or silica beads and the solid carrier carrying the molecule tag is magnetic beads, colloidal beads, or silica beads.

* * * * *

SEQUENCE LISTING

```
<160> NUMBER OF SEQ ID NOS: 28

<210> SEQ ID NO 1
<211> LENGTH: 35
<212> TYPE: DNA
<213> ORGANISM: Artificial Sequence
<220> FEATURE:
<223> OTHER INFORMATION: Linker-F

<400> SEQUENCE: 1
cttccggcag aacgacatgg ctacgaaaaa aaaaa                               35

<210> SEQ ID NO 2
<211> LENGTH: 20
<212> TYPE: DNA
<213> ORGANISM: Artificial Sequence
<220> FEATURE:
<223> OTHER INFORMATION: Linker-R

<400> SEQUENCE: 2
cgtagccatg tcgttctgcc                                               20

<210> SEQ ID NO 3
<211> LENGTH: 26
<212> TYPE: DNA
<213> ORGANISM: Artificial Sequence
<220> FEATURE:
<223> OTHER INFORMATION: 1-F
<220> FEATURE:
<221> NAME/KEY: misc_feature
<222> LOCATION: (1)..(10)
<223> OTHER INFORMATION: n is a, c, g, or t

<400> SEQUENCE: 3
nnnnnnnnnn accctgacta ggtcgc                                        26

<210> SEQ ID NO 4
<211> LENGTH: 37
<212> TYPE: DNA
```

```
<213> ORGANISM: Artificial Sequence
<220> FEATURE:
<223> OTHER INFORMATION: 1-R
<220> FEATURE:
<221> NAME/KEY: misc_feature
<222> LOCATION: (22)..(31)
<223> OTHER INFORMATION: n is a, c, g, or t

<400> SEQUENCE: 4
ggaaggcgac ctagtcaggg tnnnnnnnnn ncgcaga                              37

<210> SEQ ID NO 5
<211> LENGTH: 69
<212> TYPE: DNA
<213> ORGANISM: Artificial Sequence
<220> FEATURE:
<223> OTHER INFORMATION: 2- F
<220> FEATURE:
<221> NAME/KEY: misc_feature
<222> LOCATION: (54)..(63)
<223> OTHER INFORMATION: n is a, c, g, or t

<400> SEQUENCE: 5
gcactgacga catgatcacc aaggatcgat agtccatgct aggcgtcgtt ttannnnnnn    60 nnntctgcg                                                            69

<210> SEQ ID NO 6
<211> LENGTH: 20
<212> TYPE: DNA
<213> ORGANISM: Artificial Sequence
<220> FEATURE:
<223> OTHER INFORMATION: 2- R
<220> FEATURE:
<221> NAME/KEY: misc_feature
<222> LOCATION: (1)..(10)
<223> OTHER INFORMATION: n is a, c, g, or t

<400> SEQUENCE: 6
nnnnnnnnnn taaaacgacg                                                20

<210> SEQ ID NO 7
<211> LENGTH: 27
<212> TYPE: DNA
<213> ORGANISM: Artificial Sequence
<220> FEATURE:
<223> OTHER INFORMATION: Linker-F

<400> SEQUENCE: 7
tttttcccgt agccatgtcg ttctgcg                                        27

<210> SEQ ID NO 8
<211> LENGTH: 16
<212> TYPE: DNA
<213> ORGANISM: Artificial Sequence
<220> FEATURE:
<223> OTHER INFORMATION: Linker-R

<400> SEQUENCE: 8
acgacatggc tacggg                                                    16

<210> SEQ ID NO 9
<211> LENGTH: 22
<212> TYPE: DNA
<213> ORGANISM: Artificial Sequence
<220> FEATURE:
<223> OTHER INFORMATION: 3-F
<220> FEATURE:
<221> NAME/KEY: misc_feature
```

```
<222> LOCATION: (1)..(10)
<223> OTHER INFORMATION: n is a, c, g, or t

<400> SEQUENCE: 9
nnnnnnnnnn acctgagatc gc                                             22

<210> SEQ ID NO 10
<211> LENGTH: 34
<212> TYPE: DNA
<213> ORGANISM: Artificial Sequence
<220> FEATURE:
<223> OTHER INFORMATION: 3-R
<220> FEATURE:
<221> NAME/KEY: misc_feature
<222> LOCATION: (19)..(28)
<223> OTHER INFORMATION: n is a, c, g, or t

<400> SEQUENCE: 10
ggaagggcga tctcaggtnn nnnnnnncg caga                                 34

<210> SEQ ID NO 11
<211> LENGTH: 53
<212> TYPE: DNA
<213> ORGANISM: Artificial Sequence
<220> FEATURE:
<223> OTHER INFORMATION: 4-F
<220> FEATURE:
<221> NAME/KEY: misc_feature
<222> LOCATION: (7)..(16)
<223> OTHER INFORMATION: n is a, c, g, or t
<220> FEATURE:
<221> NAME/KEY: misc_feature
<222> LOCATION: (22)..(31)
<223> OTHER INFORMATION: n is a, c, g, or t

<400> SEQUENCE: 11
ccttccnnnn nnnnnncgat gnnnnnnnnn nttttttttt tttttttttt ttv           53

<210> SEQ ID NO 12
<211> LENGTH: 15
<212> TYPE: DNA
<213> ORGANISM: Artificial Sequence
<220> FEATURE:
<223> OTHER INFORMATION: 4-R
<220> FEATURE:
<221> NAME/KEY: misc_feature
<222> LOCATION: (6)..(15)
<223> OTHER INFORMATION: n is a, c, g, or t

<400> SEQUENCE: 12
catcgnnnnn nnnnn                                                     15

<210> SEQ ID NO 13
<211> LENGTH: 21
<212> TYPE: DNA
<213> ORGANISM: Artificial Sequence
<220> FEATURE:
<223> OTHER INFORMATION: TSO primer
<220> FEATURE:
<221> NAME/KEY: misc_feature
<222> LOCATION: (19)..(20)
<223> OTHER INFORMATION: g is GMP
<220> FEATURE:
<221> NAME/KEY: misc_feature
<222> LOCATION: (21)
<223> OTHER INFORMATION: g is a locked nucleic acid (LNA)

<400> SEQUENCE: 13
cgtagccatg tcgttctggg g                                              21
```

<210> SEQ ID NO 14
<211> LENGTH: 18
<212> TYPE: DNA
<213> ORGANISM: Artificial Sequence
<220> FEATURE:
<223> OTHER INFORMATION: ISO primer

<400> SEQUENCE: 14
cgtagccatg tcgttctg                                                  18

<210> SEQ ID NO 15
<211> LENGTH: 73
<212> TYPE: DNA
<213> ORGANISM: Artificial Sequence
<220> FEATURE:
<223> OTHER INFORMATION: Transposon 1F

<400> SEQUENCE: 15
cctagcatgg actatcgatc cttggtgatc atgtcgtcag tgcttgtctt cctaagatgt    60
gtataagaga cag                                                       73

<210> SEQ ID NO 16
<211> LENGTH: 19
<212> TYPE: DNA
<213> ORGANISM: Artificial Sequence
<220> FEATURE:
<223> OTHER INFORMATION: Transposon 1R

<400> SEQUENCE: 16
ctgtctctta tacacatct                                                 19

<210> SEQ ID NO 17
<211> LENGTH: 41
<212> TYPE: DNA
<213> ORGANISM: Artificial Sequence
<220> FEATURE:
<223> OTHER INFORMATION: Transposon 2F

<400> SEQUENCE: 17
gagacgttct cgactcagca gaagatgtgt ataagagaca g                        41

<210> SEQ ID NO 18
<211> LENGTH: 19
<212> TYPE: DNA
<213> ORGANISM: Artificial Sequence
<220> FEATURE:
<223> OTHER INFORMATION: Transposon 2R

<400> SEQUENCE: 18
ctgtctctta tacacatct                                                 19

<210> SEQ ID NO 19
<211> LENGTH: 43
<212> TYPE: DNA
<213> ORGANISM: Artificial Sequence
<220> FEATURE:
<223> OTHER INFORMATION: Blocker 1

<400> SEQUENCE: 19
cctagcatgg actatcgatc cttggtgatc atgtcgtcag tgc                      43

<210> SEQ ID NO 20
<211> LENGTH: 42
<212> TYPE: DNA
<213> ORGANISM: Artificial Sequence
<220> FEATURE:
<223> OTHER INFORMATION: Primer 3

<400> SEQUENCE: 20
cgtagccatg tcgttctgcc ggaagggcga cctagtcagg gt        42

<210> SEQ ID NO 21
<211> LENGTH: 18
<212> TYPE: DNA
<213> ORGANISM: Artificial Sequence
<220> FEATURE:
<223> OTHER INFORMATION: Primer 1

<400> SEQUENCE: 21
cgtagccatg tcgttctg        18

<210> SEQ ID NO 22
<211> LENGTH: 22
<212> TYPE: DNA
<213> ORGANISM: Artificial Sequence
<220> FEATURE:
<223> OTHER INFORMATION: Primer 2

<400> SEQUENCE: 22
gagacgttct cgactcagca ga        22

<210> SEQ ID NO 23
<211> LENGTH: 24
<212> TYPE: DNA
<213> ORGANISM: Artificial Sequence
<220> FEATURE:
<223> OTHER INFORMATION: ISO primer
<220> FEATURE:
<221> NAME/KEY: misc_feature
<222> LOCATION: (5)..(6)
<223> OTHER INFORMATION: n is deoxyuracil (dU)

<400> SEQUENCE: 23
aagcnncgta gccatgtcgt tctg        24

<210> SEQ ID NO 24
<211> LENGTH: 16
<212> TYPE: DNA
<213> ORGANISM: Artificial Sequence
<220> FEATURE:
<223> OTHER INFORMATION: Oligo for double-strand synthesis

<400> SEQUENCE: 24
tttttttttt tttttt        16

<210> SEQ ID NO 25
<211> LENGTH: 40
<212> TYPE: DNA
<213> ORGANISM: Artificial Sequence
<220> FEATURE:
<223> OTHER INFORMATION: TSO primer
<220> FEATURE:
<221> NAME/KEY: misc_feature
<222> LOCATION: (38)..(39)
<223> OTHER INFORMATION: g is GMP
<220> FEATURE:
<221> NAME/KEY: misc_feature
<222> LOCATION: (40)
<223> OTHER INFORMATION: g is a locked nucleic acid (LNA)

<400> SEQUENCE: 25
ggaaacagct atgaccatgc gtagccatgt cgttctgggg        40

```
<210> SEQ ID NO 26
<211> LENGTH: 18
<212> TYPE: DNA
<213> ORGANISM: Artificial Sequence
<220> FEATURE:
<223> OTHER INFORMATION: ISO primer

<400> SEQUENCE: 26
cgtagccatg tcgttctg                                                18

<210> SEQ ID NO 27
<211> LENGTH: 19
<212> TYPE: DNA
<213> ORGANISM: Artificial Sequence
<220> FEATURE:
<223> OTHER INFORMATION: PCR primer

<400> SEQUENCE: 27
ggaaacagct atgaccatg                                               19

<210> SEQ ID NO 28
<211> LENGTH: 24
<212> TYPE: DNA
<213> ORGANISM: Artificial Sequence
<220> FEATURE:
<223> OTHER INFORMATION: Oligo for single-strand cyclization reaction

<400> SEQUENCE: 28
gacatggcta cgggaaacag ctat                                         24
```